US009861710B1

(12) United States Patent
Ruckh et al.

(10) Patent No.: US 9,861,710 B1
(45) Date of Patent: Jan. 9, 2018

(54) COMPOSITE PARTICLES, METHODS, AND IN VIVO DIAGNOSTIC SYSTEM

(71) Applicant: Verily Life Sciences LLC, Mountain View, CA (US)

(72) Inventors: Timothy Tordella Ruckh, Mountain View, CA (US); Kimberly Kam, Mountain View, CA (US); Jerrod Joseph Schwartz, San Francisco, CA (US); Vasiliki Demas, Mountain View, CA (US); Andrew Peter Homyk, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 148 days.

(21) Appl. No.: 14/599,435

(22) Filed: Jan. 16, 2015

(51) Int. Cl.
*A61K 49/00* (2006.01)
*B29B 9/10* (2006.01)
(Continued)

(52) U.S. Cl.
CPC ............ *A61K 49/0054* (2013.01); *A61B 5/05* (2013.01); *A61B 5/145* (2013.01);
(Continued)

(58) Field of Classification Search
CPC ............ A61B 5/14532; A61B 5/14546; A61B 5/1486; A61B 5/14539; A61B 5/0031
See application file for complete search history.

(56) References Cited

U.S. PATENT DOCUMENTS 4,603,209 A 7/1986 Tsien et al.
4,714,763 A 12/1987 Theodoropulos
(Continued)

FOREIGN PATENT DOCUMENTS

EP 1 065 250 A1 1/1999
EP 1790977 A1 5/2007
(Continued)

OTHER PUBLICATIONS

Dubach, et al., "Fluorescent Ion-Selective Nanosensors for Intracellular Analysis with Improved Lifetime and Size", Nano Lett., May 11, 2007, vol. 7(6), pp. 1827-1831, DOI:10.1021/nl0707860. (Abstract only).

(Continued)

*Primary Examiner* — Eric Winakur
*Assistant Examiner* — Marjan Fardanesh
(74) *Attorney, Agent, or Firm* — McDonnell Boehnen Hulbert & Berghoff LLP

(57) ABSTRACT

A system is provided which includes the composite nanoparticles configured to bind with a target analyte, the composite nanoparticles including a polymer matrix; nanoparticles at least one type; reporter labels at least one type; and targeting entities at least one type, wherein the nanoparticles at least one type, the reporter labels at least one type and the targeting entities at least one type are encapsulated in the polymer matrix; a body-mountable device mounted on an external surface of a living body and configured to detect a target analyte binding response signal transmitted through the external surface, wherein the target analyte binding response signal is related to binding of the composite nanoparticles with one or more target analytes; and a processor configured to non-invasively detect the one or more target analytes based on the target analyte response signal. Composite nanoparticles and methods for use and for making are also provided.

5 Claims, 21 Drawing Sheets

(51) Int. Cl.
*A61B 5/145* (2006.01)
*A61B 5/05* (2006.01)
*B29L 31/00* (2006.01)

(52) U.S. Cl.
CPC ............ *A61K 49/0013* (2013.01); *B29B 9/10* (2013.01); *B29L 2031/00* (2013.01)

(56) References Cited

U.S. PATENT DOCUMENTS

| | | |
|---|---|---|
| 4,774,339 A | 9/1988 | Haugland et al. |
| 4,810,636 A | 3/1989 | Corey |
| 4,812,409 A | 3/1989 | Babb et al. |
| 4,849,362 A | 7/1989 | DeMarinis et al. |
| 4,945,171 A | 7/1990 | Haugland et al. |
| 4,981,977 A | 1/1991 | Southwick et al. |
| 5,132,432 A | 7/1992 | Haugland et al. |
| 5,187,288 A | 2/1993 | Kang et al. |
| 5,227,487 A | 7/1993 | Haugland et al. |
| 5,242,805 A | 7/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,433,896 A | 7/1995 | Kang et al. |
| 5,442,045 A | 8/1995 | Haugland et al. |
| 5,451,343 A | 9/1995 | Neckers et al. |
| 5,459,276 A | 10/1995 | Kuhn et al. |
| 5,478,860 A | 12/1995 | Wheeler et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,627,027 A | 5/1997 | Waggoner |
| 5,696,157 A | 12/1997 | Wang et al. |
| 5,798,276 A | 8/1998 | Haugland et al. |
| 5,808,044 A | 9/1998 | Brush et al. |
| 5,830,912 A | 11/1998 | Gee et al. |
| 5,846,737 A | 12/1998 | Kang |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,162,931 A | 12/2000 | Gee et al. |
| 6,229,055 B1 | 5/2001 | Klaubert et al. |
| 6,339,392 B1 | 1/2002 | Ashihara |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,778,316 B2 | 8/2004 | Halas et al. |
| 6,974,873 B2 | 12/2005 | Leung et al. |
| 6,977,305 B2 | 12/2005 | Leung et al. |
| 7,253,004 B2 | 8/2007 | Vossmeyer et al. |
| 7,704,754 B2 | 4/2010 | Malak |
| 8,217,108 B2 | 7/2012 | Cooper et al. |
| 8,246,968 B2 | 8/2012 | Zale et al. |
| 8,344,054 B2 | 1/2013 | Sun et al. |
| 8,821,837 B2 | 9/2014 | Perez et al. |
| 2004/0142025 A1 | 7/2004 | MacLachlan et al. |
| 2007/0029195 A1 | 2/2007 | Li et al. |
| 2009/0013609 A1 | 1/2009 | Gupta et al. |
| 2009/0061226 A1 | 3/2009 | Banin et al. |
| 2010/0261808 A1 | 10/2010 | Schadler et al. |
| 2011/0140580 A1 | 6/2011 | Yang et al. |
| 2012/0052286 A1 | 3/2012 | Norwood et al. |
| 2012/0164079 A1 | 6/2012 | Sharma |
| 2012/0252002 A1 | 10/2012 | Pinto De Melo et al. |
| 2012/0301870 A1 | 11/2012 | Dordick et al. |
| 2013/0037977 A1 | 2/2013 | Burke et al. |
| 2013/0130348 A1* | 5/2013 | Gu ........................ A61K 9/5153 435/188 |
| 2013/0251943 A1 | 9/2013 | Pei et al. |
| 2013/0323182 A1* | 12/2013 | Hyeon ................. A61K 49/186 424/9.322 |
| 2014/0138863 A1* | 5/2014 | Cheng ................. B81C 1/00214 264/8 |

FOREIGN PATENT DOCUMENTS

| | | | |
|---|---|---|---|
| EP | 1278061 B1 | 2/2011 | |
| EP | 2527392 A1 | 11/2012 | |
| EP | 2664192 A1 | 10/2013 | |
| EP | 2698066 A2 | 2/2014 | |
| WO | 97/40104 A1 | 10/1997 | |
| WO | 99/51702 A1 | 10/1999 | |
| WO | 01/05373 A1 | 1/2001 | |
| WO | 01/21624 A1 | 3/2001 | |
| WO | 02/26891 A1 | 4/2002 | |
| WO | 2005/085339 A1 | 9/2005 | |
| WO | 2008/070459 A2 | 6/2008 | |
| WO | 2009/135325 A1 | 11/2009 | |
| WO | 2011/034570 A1 | 3/2011 | |
| WO | WO 2012151593 A1 * | 11/2012 | ........... A61B 5/0075 |
| WO | 2013/013030 A2 | 1/2013 | |
| WO | 2013/109057 A1 | 7/2013 | |
| WO | 2014/037498 A2 | 3/2014 | |
| WO | 2014/057432 A2 | 4/2014 | |
| WO | WO 2015100373 A2 * | 7/2015 | ............. C12N 15/09 |

OTHER PUBLICATIONS

Lee, et al., "In Vitro and In Vivo Evaluation of Structure-Stability Relationships of 111In- and 67Ga-labeled Antibody via 1B4M or C-NOTA Chelates", Nuclear Medicine and Biology, Apr. 1997, vol. 24(3), pp. 225-230. (Abstract only).

Ozer, et al., "New Technologies Provide Quantum Changes in the Scale, Speed, and Success of SELEX Methods and Aptamer Characterization", Molecular Therapy Nucleic Acids, Aug. 5, 2014, vol. 3, pp. 1-36, doi:10.1038/mtna2014.34.

Quinn, et al., "Biocompatible, Glucose-Permeable Hydrogel for In Situ Coating of Implantable Biosensiors", Biomaterials, Dec. 1997, vol. 18(24), pp. 1665-1670. (Abstract only).

Quinn, C.P., et al., "Photo-Crosslinked Copolymers of 2-Hydroxyethyl Methacrylate, Poly(ethylene glycol) Tetra-Acrylate and Ethylene Dimethacrylate for Improving Biocompatibility of Biosensors", Biomaterials, Mar. 1995, vol. 16 (5), pp. 389-396. (Abstract only).

Richieri, Gary V., et al.,"A Flourescently Labeled Intestinal Fatty Acid Binding Protein", J. Biol. Chem., Nov. 25, 1992, vol. 267(33), pp. 23495-23501.

Stoltenburg, et al., "SELEX—A (R)evolutionary Method to Generate High-Affinity Nucleic Acid Ligands", Biomolecular Engineering, Jun. 1, 2007, vol. 24, pp. 381-403, doi:10.1016/j.bioeng.2007.06.001.

Ghandehari, H., et al., "Biodegradable and pH Sensitive Hydrogels: Synthesis by a Polymer-Polymer Reaction", J. Macromol. Chem. Phys., Mar. 1996, vol. 197(3), pp. 965-980. (Abstract only).

Ishihara, K., et al., "Glucose Induced Permeation Control of Insulin through a Complex Membrane Consisting of Immobilized Glucose Oxidase and a Poly(amine)", Polymer J., 1984, vol. 16(8), pp. 625-631.

Ruckh, T.T., et al., "Implantable Nanosensors: Toward Continuous Physiologic Monitoring", Anal. Chem., 2014, vol. 86, pp. 1314-1323, dx.doi.org/10.1021/ac402688k.

Hanemann, T., et al., "Polymer-Nanoparticle Composites: From Synthesis to Modern Applications", Materials, 2010, vol. 3, pp. 3468-3517, doi:10.3390/ma3063468.

* cited by examiner

E1 - FIRST ENZYME IN CASCADE
M1 - MODULATOR FOR E1
E2 - SECOND ENZYME IN CASCADE
M2 - MODULATOR FOR E2
F1 - FLUOROPHORE 1
F2 - FLUOROPHORE 2

COMPOSITE PARTICLES, METHODS, AND IN VIVO DIAGNOSTIC SYSTEM

BACKGROUND

Unless otherwise indicated herein, the materials described in this section are not prior art to the claims in this application and are not admitted to be prior art by inclusion in this section.

A number of diagnostic methods have been developed to evaluate physiological conditions of a person by detecting and/or measuring one or more analytes in a person's blood or other bodily fluids or tissue. One or more target analytes could be any analytes that, when present in or absent from the blood, or present at a particular concentration or range of concentrations, may be indicative of a medical condition or health state of the person. These target analytes could include enzymes, reagents, hormones, proteins, cells, ions, e.g., sodium, potassium, calcium, or chloride, or molecules such creatine, urea, and carbohydrates, e.g., glucose. While many of the diagnostic methods that employ labeled agents are useful, they can be improved.

Much effort has been devoted into developing nanoparticles as vehicles for diagnosis, imaging as well as delivery of agents for treatment of disease. Nanoparticles have been conjugated to drugs, imaging agents or other substances that can be delivered to specific sites either by active targeting or by size-dependent passive targeting. However, one challenge associated with the use of nanoparticles is that individual nanoparticles may lack a set of desired chemical, physical or biological properties and it may be difficult to engineer multiple complex properties into a single particle type. Accordingly, there is a need for improved particles have a predetermined tailored set of properties that are useful in diagnostic, imaging and/or therapeutic methods to determine or monitor a medical condition or a person's state of health.

SUMMARY

One aspect of the present disclosure provides a composite particle. The composite particle includes (i) a polymer matrix; (ii) nanoparticles at least one type; (iii) reporter labels at least one type; and (iv) targeting entities at least one type, wherein the nanoparticles at least one type, the reporter labels at least one type and targeting entities at least one type are encapsulated in the polymer matrix. In one embodiment, the composite particle further includes a linker, wherein at least one type of reporter label, the least one type of targeting entity, or both are associated with the linker. In other embodiments, at least one of the at last one type of reporter label, the at least one type of targeting entity, or both are associated with the at least one type of nanoparticles. In another embodiment, the composite particle is a composite nanoparticle or a composite microparticle. In some embodiments, the nanoparticles comprise a polymer material, a metal, or a magnetic material.

In another aspect, the present disclosure provides a method for preparing a composite particle. The method including the steps of: (a) casting a solution of nanoparticles at least one type, reporter labels at least one type, targeting entities at least one type and matrix precursors into a mold, the mold including a plurality of nanowells; (b) exposing the cast solution to a curing stimulus to form the superparticles; and (c) recovering the superparticles from the mold. In some embodiments, the method further includes the step of thermally annealing the nanoparticles in the cast solution in the wells.

In another aspect, the present disclosure provides a system. The system includes: (a) a wearable device comprising a mount configured to mount the wearable device on an external surface of a living body and a detector configured to detect an analyte response signal transmitted from tissue through the external surface, wherein the tissue contains composite particle including (i) a polymer matrix; (ii) nanoparticles at least one type; (iii) reporter labels at least one type; and (iv) targeting entities at least one type, wherein the nanoparticles at least one type, the reporter labels at least one type and the targeting entities are encapsulated in the polymer matrix; and (c) a processor configured to determine a presence or absence of the one or more target analytes based on the analyte response signal. In some embodiments, the system further includes a modulation source configured to modulate the analyte response signal differently than a background signal. In other embodiments, the system further includes an interrogating signal source configured to apply an interrogating signal to the tissue, wherein the analyte response signal is transmitted in response to the interrogating signal.

In a further aspect, the present disclosure provides a method including: (a) introducing composite particles into the living body, the composite particle including (i) a polymer matrix; (ii) nanoparticles at least one type; (iii) reporter labels at least one type; and (iv) targeting entities at least one type, wherein the nanoparticles at least one type, the reporter labels at least one type and the targeting entities are encapsulated in the polymer matrix; wherein the composite particles are configured to bind with one or more target analytes, wherein presence or absence of the one or more target analytes in the living body is correlated with the biological state of the living body; (b) detecting, by a wearable device mounted on an external surface of the living body, a signal transmitted from the living body, wherein the signal includes an analyte response signal that is related to binding of the one or more target analytes with the composite particles; and (c) determining a presence or absence of the one or more target analytes based on the analyte response signal.

These as well as other aspects, advantages, and alternatives, will become apparent to those of ordinary skill in the art by reading the following detailed description, with reference where appropriate to the accompanying drawings.

DETAILED DESCRIPTION

Figure 1A:
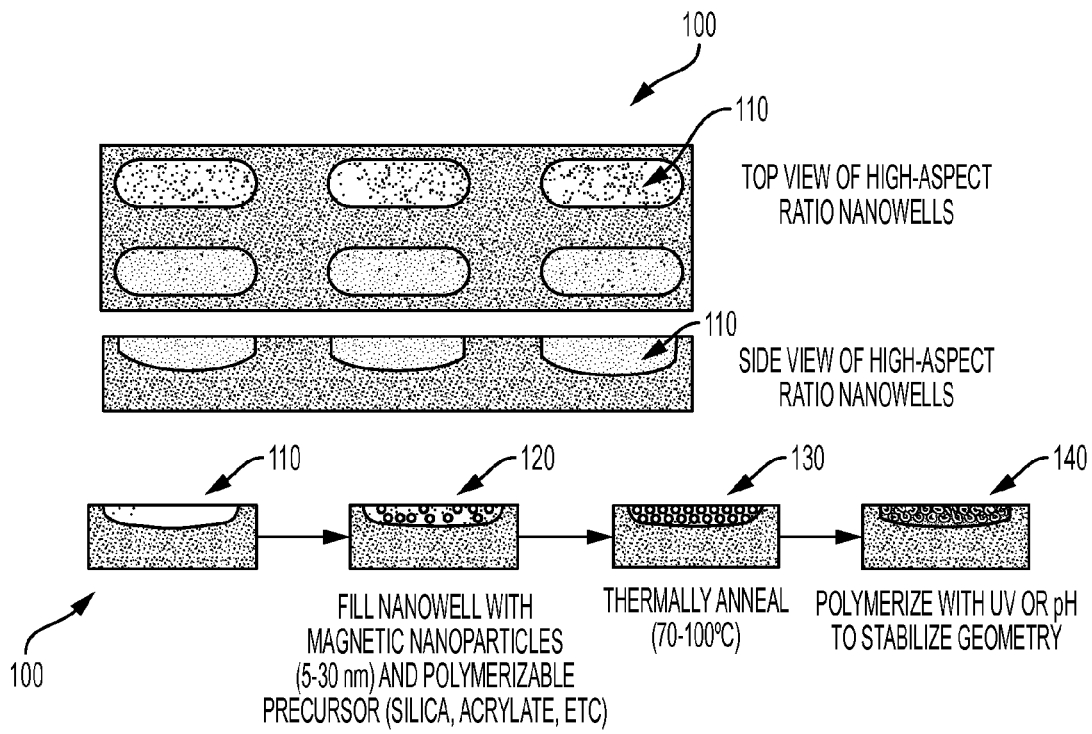
FIG. 1(a) illustrates the process for preparing a composite conjugate using one type of nanoparticles; and 1(b) illustrates a process for preparing a composite conjugate which employs two different types of nanoparticles.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Composite Particles

Composite particles (used interchangeably with the term "superparticles") can be defined as a heterogeneous composition comprising a polymer matrix and a plurality of embedded nanoparticles, reporter labels, and targeting entities with different desired properties. The resulting superparticle has many or all of the desired individual properties of its constituents and can take on enhanced properties associated with, for instance, carefully spaced photonic nanoparticles, fluorescent dyes, sensing chemistries, or reports. The signals produced by the superparticles may be optical, magnetic, acoustic, or a combination thereof and may be modulated by sensing chemistries recognizing a target analyte of interest. The pre-determined manipulation of the composition, shape, and size will allow for the engineering of multiple complex properties into a single particle type (superparticle) and will define the superparticle's final physicochemical and imaging properties. The composite particles of the present disclosure have multiple uses including use as sensors, e.g, biosensors for the detection of target analytes; delivery vehicles for imaging agents, pharmaceuticals and the like; and catalysis.

In one embodiment, the composite particle includes (i) a polymer matrix; (ii) nanoparticles at least one type; (iii) reporter labels at least one type; and (iv) targeting entities at least one type, wherein the nanoparticles at least one type, the reporter labels at least one type and the targeting entities at least one type are encapsulated in the polymer matrix. In one embodiment, the composite particle further includes a linker, wherein the reporter labels at least one type, the targeting entities at least one type, or both are associated with the linker. In another embodiment, at least one of the reporter labels at least one type, the targeting entities at least one type, or both are associated with the at least one type of nanoparticles. In another embodiment, the composite particle is a composite nanoparticle or a composite microparticle. In some embodiments, the nanoparticles comprise a polymer material, a metal, or a magnetic material. In another embodiments, the composite particle includes two or more types of nanoparticles.

A. Nanoparticles

The term "nanoparticle" refers to any particle having a diameter of less than 1000 nanometers (nm). Representative examples of nanoparticles include, without limitation, quantum dots, plasmonic nanoparticles such as gold or silver nanoparticles, upconverting nanocrystals, iron oxide nanoparticles or other superparamagnetic or magnetic particles, silica, liposomes, micelles, carbon nanotubes, doped or undoped graphene, graphene oxide, nanodiamonds, titania, alumina, and metal oxides. In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. Typically the nanoparticles can have a longest straight dimension (e.g., diameter) of less than 1000 nm, 900 nm, 800 nm, 700 nm, 600 nm, 500 nm, 400 nm, 300 nm, 200 nm or less. In some embodiments, the nanoparticles can have a diameter of 200 nm or less. In other embodiments, the nanoparticles have a diameter of 100 nm or less. Smaller nanoparticles, e.g., having diameters of 50 nm or less, e.g., 5 nm-30 nm, are used in some embodiments.

In one embodiment, nanoparticles are quantum dots, i.e., bright, fluorescent nanocrystals with physical dimensions small enough such that the effect of quantum confinement gives rise to unique optical and electronic properties. In certain embodiments, optically detectable nanoparticles are metal nanoparticles. Metals of use in the nanoparticles include, but are not limited to, gold, silver, iron, cobalt, zinc, cadmium, nickel, gadolinium, chromium, copper, manganese, palladium, tin, and alloys and/or oxides thereof. In some embodiments, magnetic nanoparticles are of use in accordance with the invention. "Magnetic nanoparticles" refers to magnetically responsive nanoparticles that contain one or more metals or oxides or hydroxides thereof.

In other embodiments, the nanoparticles are made from polymers or lipids See for instance, EP 2644 192; U.S. Pat. No. 8,246,968; U.S. Patent Publication No. 2013/0037977; U.S. Pat. No. 5,478,860; U.S. Patent Publ. No. 2004/0142025; International Patent Publication Nos. WO 01/05373, 2014/057432, and 2014/037498; and EP 2698066, which are incorporated by reference in their entirety.

In other embodiments, the nanoparticle comprises a bulk material that is not intrinsically fluorescent, luminescent, plasmon resonant, or magnetic. The nanoparticle comprises one or more fluorescent, luminescent, or magnetic moieties. For example, the nanoparticle may comprise QDs, fluorescent or luminescent organic molecules, or smaller nanoparticles of a magnetic material. In other embodiments, the nanoparticles are made from polymers.

In some embodiments, a nanoparticle composed in part or in whole of an organic polymer is used. A wide variety of organic polymers and methods for forming nanoparticles therefrom are known in the art. For example, nanoparticles composed at least in part of polymethylmethacrylate, polyacrylamide, poly(vinyl chloride), carboxylated poly(vinyl chloride), or poly(vinyl chloride-co-vinyl acetate-co-vinyl alcohol) may be used. Optionally the nanoparticle comprises one or more plasticizers or additives. Co-polymers, block co-polymers, and/or grafted co-polymers can be used.

In some embodiments, the nanoparticles can be labeled with any suitable reporter label including, without limitation, fluorescent and luminescent moieties such as a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g. Valeur, B., "Molecular Fluorescence: Principles and Applications," John Wiley and Sons, 2002; Handbook of Fluorescent Probes and Research Products, Molecular Probes, 9th edition, 2002; and The Handbook-A Guide to Fluorescent Probes and Labeling Technologies, Invitrogen, $10^{th}$ edition). In some embodiments, the labels can include non-fluorescent dyes or nanoparticles that can act as quenchers for fluorophores. Such nanoparticle labels may quench dynamically by distance modulation or molecular structure modulation in response to a change in the local environment or molecular recognition event.

In some embodiments, the nanoparticles can be biocompatible and/or biodegradable. As used herein, the term "biocompatible" refers to substances that are not toxic to cells or are present in levels that are not toxic to cells. In some embodiments, a substance is considered to be "biocompatible" if its addition to cells in vivo does not induce inflammation and/or other adverse effects in vivo. In other embodiments, the materials composing the nanoparticles can be generally recognized as safe (GRAS) or FDA-approved materials. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death. In general, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, a nanoparticle which is biocompatible and/or biodegradable may be associated with a targeting entity and/or an agent to be delivered that is not biocompatible, is not biodegradable, or is neither biocompatible nor biodegradable. In some embodiments, a nanoparticle which is biocompatible and/or biodegradable may be associated with agent to be delivered is also biocompatible and/or biodegradable.

Nanoparticles can have a coating layer. Use of a biocompatible coating layer can be advantageous, e.g., if the nanoparticles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, and other nanoparticles, etc. Coatings may be applied or assembled in a variety of ways such as by dipping, using a layer-by-layer technique, self-assembly, conjugation, etc.

In some embodiments, the nanoparticles may optionally comprise one or more dispersion media, surfactants, release-retarding ingredients, or other pharmaceutically acceptable excipient. In some embodiments, nanoparticles may optionally comprise one or more plasticizers or additives.

In some embodiments, nanoparticles may be intrinsically magnetic nanoparticles. In some embodiments, fluorescent or luminescent nanoparticles, nanoparticles that comprise fluorescent or luminescent moieties, and plasmon resonant nanoparticles can be useful. In some embodiments, the nanoparticles have detectable optical and/or magnetic properties. In one embodiment, an optically detectable nanoparticle is one that can be detected within a living cell using optical means compatible with cell viability. In another embodiment, an optically detectable nanoparticle is one that can be detected within a living cell using optical means compatible with cell viability in a biological setting and that do not permanently comprise the integrity or viability of the cells or tissues. Optical detection is accomplished by detecting the scattering, emission, and/or absorption of light that falls within the optical region of the spectrum, i.e., that portion of the spectrum extending from approximately 400 nm to several microns. Optionally a sample containing cells is exposed to a source of electromagnetic energy. In some embodiments, absorption of electromagnetic energy (e.g. light of a given wavelength) by the nanoparticle or a component thereof is followed by the emission of light at longer wavelengths, and the emitted light is detected. In some embodiments, scattering of light by the nanoparticles is detected. In certain embodiments, light falling within the visible portion of the electromagnetic spectrum, i.e., the portion of the spectrum that is detectable by the human eye (approximately 400 nm to approximately 700 nm) is detected. In some embodiments, light that falls within the infrared or ultraviolet region of the spectrum is detected.

The optical property can be a feature of an absorption, emission, or scattering spectrum or a change in a feature of an absorption, emission, or scattering spectrum. The optical property can be a visually detectable feature such as, for example, color, apparent size, or visibility (i.e. simply whether or not the particle is visible under particular conditions). Features of a spectrum include, for example, peak wavelength or frequency (wavelength or frequency at which maximum emission, scattering intensity, extinction, absorption, etc. occurs), peak magnitude (e.g., peak emission value, peak scattering intensity, peak absorbance value, etc.), peak width at half height, or metrics derived from any of the foregoing such as ratio of peak magnitude to peak width. Certain spectra may contain multiple peaks, of which one is typically the major peak and has significantly greater intensity than the others. Each spectral peak has associated features. Typically, for any particular spectrum, spectral features such as peak wavelength or frequency, peak magnitude, peak width at half height, etc., are determined with reference to the major peak. The features of each peak, number of peaks, separation between peaks, etc., can be considered to be features of the spectrum as a whole. The foregoing features can be measured as a function of the direction of polarization of light illuminating the nanoparticles; thus polarization dependence can be measured. Features associated with hyper-Rayleigh scattering can be measured. Fluorescence detection can include detection of fluorescence modes. Luminescence detection can also be useful for optical imaging purposes. Raman scattering can also be useful as well.

In various embodiments, intrinsically fluorescent or luminescent nanoparticles, nanoparticles that comprise fluorescent or luminescent moieties, plasmon resonant nanoparticles, and magnetic nanoparticles are among the detectable nanoparticles that can be used. Such nanoparticles can have a variety of different shapes including variety of different shapes including spheres, oblate spheroids, cylinders, ovals, ellipses, shells, cubes, cuboids, cones, pyramids, rods (e.g., cylinders or elongated structures having a square or rectangular cross-section), tetrapods (nanoparticles having four leg-like appendages), triangles, prisms, etc. Nanoparticles can be also solid or hollow and can comprise one or more layers (e.g., nanoshells, nanorings, etc.). Nanoparticles may have a core/shell structure, wherein the core(s) and shell(s) can be made of different materials. Nanoparticles may comprise gradient or homogeneous alloys. Nanoparticles may be a composite made of two or more materials, of which one, more than one, or all of the materials possess magnetic properties, electrically detectable properties, and/or optically detectable properties.

In general, the nanoparticles should have dimensions small enough to prepare nano- and micro-sized composite particles. Typically the nanoparticles have a longest straight dimension (e.g., diameter) of 200 nm or less. In some embodiments, the nanoparticles have a diameter of 100 nm or less. For nano-sized composite particles, smaller nanoparticles, e.g. having diameters of 50 nm or less, e.g., 5 nm-30 nm, are useful.

B. Targeting Entity

In one embodiment, the superparticle includes a nanoparticle and/or a reporter label associated with one or more targeting entities. In other embodiments, the superparticle includes a linker that is associated with one or more targeting entities. In general, a "targeting entity" is any entity that binds to a component (also referred to as a "target" or a "marker") associated with a bodily fluid such as blood, an organ, tissue, cell, subcellular locale, and/or extracellular matrix component. A targeting entity may be an antibody, nucleic acid (e.g., aptamer, DNA barcodes, DNA dendrimers, DNA-zyme, RNA-zyme), polypeptide, glycoprotein, carbohydrate, lipid, enzyme, nanobodies, ScFv, an ionophore, small molecule recognition element, a charge carrying small molecule, etc. For example, a targeting entity can be a nucleic acid targeting entity (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting entity may be a naturally occurring or synthetic ligand for a cell surface receptor, e.g., a growth factor, hormone, LDL, transferrin, etc. A targeting entity can be an antibody, which term is intended to include antibody fragments, characteristic portions of antibodies, single chain antibodies, etc. Synthetic binding proteins such as affibodies, etc., can be used. Peptide targeting entities can be identified, e.g., using procedures such as phage display. This widely used technique has been used to identify cell specific ligands for a variety of different cell types.

In one embodiment, the targeting entities bind to a target analyte, e.g. glucose or ion such as sodium, potassium, calcium, or chloride) in a bodily fluid such as blood, interstitium, or perspiration. In other embodiments, targeting entities bind to an organ, tissue, cell, extracellular matrix component, and/or intracellular compartment that is associated with a specific developmental stage or a specific disease state (i.e. a "target" or "marker"). In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In some embodiments, a target is more prevalent, accessible, and/or abundant in a diseased locale (e.g. organ, tissue, cell, subcellular locale, and/or extracellular matrix component) than in a healthy locale.

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, metal coordination, etc.). In some embodiments, a sufficient number of weaker interactions can provide sufficient stability for moieties to remain physically associated.

In one embodiment, the targeting agent is an antibody. As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" refers to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids. Antibodies to many markers are known to those of skill in the art and can be obtained commercially or readily produced by known methods such as using phage-display or yeast-display technology.

In another embodiment, the targeting agent is an aptamer. Sometimes referred to as "synthetic antibodies," aptamers are pre-selected single-stranded oligonucleotide (e.g., DNA or RNA) or peptide molecules that bind to specific target molecules including proteins and peptides with affinities and specificities that are comparable to antibodies. These molecules can assume a variety of shapes due to their propensity to form helices and single-stranded loops with specific binding pockets, explaining their versatility in binding to diverse targets. Their specificity and characteristics are not directly determined by their primary sequence but by their tertiary structure which is analogous to the globular shape of tRNA. Aptamers have a wide range of applications including diagnostics and therapeutics and can be chemically synthesized using known techniques. Furthermore, aptamers can offer a number of advantages over traditional antibodies including avoiding the need to specifically know the precise epitopes or biomarkers themselves. Finally, aptamers are typically non-immunogenic, easy to synthesize, characterize, modify and exhibit high specificity and affinity for their target antigen.

By using a variety of selection techniques, aptamers can be selected to find targets, e.g., on a surface or inside a cell of interest, without the need to identify the precise biomarker or epitopes themselves. In many cases, the aptamer identification process can begin with a large random pool of oligonucleotides or peptides that are systematically subjected to iterative negative and positive rounds of selection against a target, e.g., a protein molecule, to separate out out low affinity or unspecific binders. The remaining aptamers in the enriched pool can be collected and propagated, e.g., PCR amplified, and used in subsequent rounds of selection. Typically anywhere from three to twenty cycles of target binding, separation, and amplification are carried out and the candidate aptamers are then characterized for binding affinity and specificity. This selection process, referred to as Systemic Evolution of Ligands by Exponential Enrichment or SELEX, is commonly used for selecting and identifying highly-targeted aptamers directed to a wide variety of targets include whole living cells. For a review of SELEX methods to screen and separate binding molecules, e.g., aptamers, from libraries of aptamers, see Stoltenburg et al. Biomolecular Engineering, 2007, Vol. 24, pp. 381-403; and Ozer et al., Molecular Therapy Nucleic Acids, 2014, Vol. 3, e183; doi:10.1038/mtna.2014.34, published on line Aug. 5, 2014. Various methods have been used for separating out the target bound and unbound aptamers including nitrocellulose filter binding, bead-based, electrophoretic, microfluidic, microarray-based, and microscopic.

C. Reporter Labels

In one embodiment, the superparticle includes a component such as the targeting entity, nanoparticles, the polymeric matrix, or a linker that can be labeled with any suitable reporter labeling moiety (also referred to as "labeling moiety", "label", "reporter" or "reporter label". A "labeling moiety" or "labels" as used herein, is intended to mean a chemical compound, molecule, ion, or particle that directly possesses or indirectly comes to possess a detectable signal. Representative examples of reporter labels include, without limitation, organic dyes, state dyes, environmentally-responsive absorbers that are sensitive to changes in oxygen, pH, and redox levels, fluorophores, phosphores, porphyrins, and conducting/responsive polymers. In some embodiments, the superparticle component can be labeled with one or more compounds or molecules such as fluorophores or autofluorescent or luminescent markers or non-optical contrast agents (e.g., acoustic impedance contrast, RF contrast and the like) or enzymes or enzyme substrates which may further assist in interrogating the superparticles in vivo. The labels can be used to indicate a conformational change of the targeting entity which can be indicative of target binding. The labeling moieties used in the current methods and compositions can be attached through any suitable means including chemical means, such as reduction, oxidation, conjugation, and condensation reactions. For example, any thiol-reactive group can be used to attach labeling moieties, e.g., a fluorophore, to a naturally occurring or engineered thiol group present in the targeting entity, e.g., aptamer or antibody. Also, for example, reactive groups present in the targeting agent can be labeled using succinimide ester derivatives of fluorophores. See Richieri, G. V. et al., J. Biol. Chem., 267: 23495-501 (1992) which is hereby incorporated by reference.

Alternatively, the targeting entity, e.g., aptamer, can be coupled to a label, e.g., a particle such as a nanoparticle, using well-known click chemistry which entails labeling the aptamer with an azide or alkyne group and coupling the labeled aptamer to an alkyne/azide group on the particle. Alternatively, the targeting entity, e.g., aptamer, may be labeled with an NH2 group and then coupled to —COOH group on the particle using 1-ethyl-3-[3-dimethylaminopropyl]carbodiimide hydrochloride (EDC or EDAC) crosslinking agent (commercially available from Thermo Fisher Scientific, Inc., Rockford, Ill., USA). In some embodiments, photocleavable linkers or spacers can be used to conjugate the targeting entity or nanoparticle to the reporter label. Photocleavable linkers are commercially available. See for instance Integrated DNA Technologies, Inc., Coralville, Iowa, USA; and Ambergen, Inc., Watertown, Mass., USA).

In one embodiment, the labeling moiety can emit an optical signal. Numerous labels are known by those of skill in the art and include, but are not limited to, particles, fluorophores, haptens, enzymes and their colorimetric, fluorogenic and chemiluminescent substrates and other labels that are described in RICHARD P, HAUGLAND, MOLECULAR PROBES HANDBOOK OF FLUORESCENT PROBES AND RESEARCH PRODUCTS (9th edition, CD-ROM, (September 2002), which is herein incorporated by reference.

A fluorophore label can be any chemical moiety that exhibits an absorption maximum at or beyond 280 nm, and when covalently attached to the superparticle component, e.g., targeting entity, or other component retains its spectral properties. Fluorophores of the present invention include, without limitation; a pyrene (including any of the corresponding derivative compounds disclosed in U.S. Pat. No. 5,132,432, incorporated by reference), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine (including any corresponding compounds in U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; 6,664,047; 6,974,873 and 6,977,305; and publications WO 02/26891, WO 97/40104, WO 99/51702, WO 01/21624; EP 1 065 250 A1, incorporated by reference), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274, 113; and 5,433,896, incorporated by reference), a xanthene (including any corresponding compounds disclosed in U.S. Pat. Nos. 6,162,931; 6,130,101; 6,229,055; 6,339,392; 5,451,343 and 6,716,979, incorporated by reference), an oxazine (including any corresponding compounds disclosed in U.S. Pat. No. 4,714,763, incorporated by reference) or a benzoxazine, a carbazine (including any corresponding compounds disclosed in U.S. Pat. No. 4,810,636, incorporated by reference), a phenalenone, a coumarin (including an corresponding compounds disclosed in U.S. Pat. Nos. 5,696, 157; 5,459,276; 5,501,980 and 5,830,912, incorporated by reference), a benzofuran (including an corresponding compounds disclosed in U.S. Pat. Nos. 4,603,209 and 4,849,362, incorporated by reference) and benzphenalenone (including any corresponding compounds disclosed in U.S. Pat. No. 4,812,409, incorporated by reference) and derivatives thereof. As used herein, oxazines include resorufins (including any corresponding compounds disclosed in U.S. Pat. No. 5,242,805, incorporated by reference), aminooxazinones, diaminooxazines, and their benzo-substituted analogs. When the fluorophore is a xanthene, the fluorophore is optionally a fluorescein, a rhodol (including any corresponding compounds disclosed in U.S. Pat. Nos. 5,227,487 and 5,442,045, incorporated by reference), or a rhodamine (including any corresponding compounds in U.S. Pat. Nos. 5,798,276; 5,846,737 and 6,562,632, incorporated by reference). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the present invention include, but are not limited to, xanthene (rhodol, rhodamine, fluorescein and derivatives thereof) coumarin, cyanine, pyrene, oxazine and borapolyazaindacene. Sulfonated and/or alkylated xanthenes, fluorinated xanthenes, sulfonated coumarins, fluorinated coumarins and sulfonated cyanines can be useful. The choice of the fluorophore will determine the absorption and fluorescence emission properties of the superparticle. Physical properties of a fluorophore label include spectral characteristics (absorption, emission and stokes shift), fluorescence intensity, lifetime, polarization and photo-bleaching rate all of which can be used to distinguish one fluorophore from another.

Binding of the superparticle to a target analyte may be detected with or without an interrogation signal input. The term "binding" is understood in its broadest sense to include any detectable interaction between the superparticle and the target analyte. For example, some superparticles may be functionalized with compounds or molecules, such as fluorophores or autofluorescent, luminescent or chemiluminescent markers, which generate a responsive signal with the input of a stimulus when the target diffuses into and binds on or within the superparticles. In other examples, the superparticles may produce a different responsive signal in their bound versus unbound state in response to an external stimulus, such as an electromagnetic, acoustic, optical, or mechanical energy.

In one embodiment, multiple analyte detection is possible. By immobilizing a plurality of target entities of different binding specificity to target analytes, each targeting entity associated directly or indirectly with distinct labels, e.g., different fluorophores, simultaneous multiple target analyte determinations can be made, thereby providing clinicians with deeper insight into the identification and assessment of health state and disease progression. The use of spectral filters and/or alternative light sources as the interrogation signal can be used to excite the label, e.g., fluorophores and detect light, e.g., fluorescent light, from the different labels, and thereby, determine the contribution of each fluorophore to the total fluorescent properties of the sample.

D. Linkers

In one embodiment, the targeting entity, the reporter label and/or any other component (e.g, imaging agent or drug) can be attached to the nanoparticles via a linking agent. In other embodiments, the targeting entity and/or the reporter can be attached to each other via a linking agent. For instance, a targeting entity and/or reporter label and nanoparticle can be conjugated via a single linking agent or multiple linking agents. For example, the targeting entity and/or reporter label and nanoparticle may be conjugated via a single multifunctional (e.g., bi-, tri-, or tetra-) linking agent or a pair of complementary linking agents. In another embodiment, the targeting agent and/or reporter label and the nanoparticle are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine (NH$_2$), hydroxyl (—OH), aldehyde (—CHO), alcohol (ROH), ketone (R$_2$CO), active hydrogen, ester, sulfhydryl (SH), phosphate (—PO$_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) Advanced Organic Chemistry, 3rd Ed., John Wiley & Sons, New York, Hermanson (1996) Bioconjugate Techniques, Academic Press, San Diego; and Feeney et al. (1982) Modification of Proteins; Advances in Chemistry Series, Vol. 198, American Chemical Society, Washington, D.C., which are incorporated by reference in their entirety.

In some embodiments, the linking agent is a chelator. For example, the chelator comprising the molecule, DOTA (DOTA=1,4,7,10-tetrakis(carboxymethyl)-1,4,7,10-tetraazacyclododecane), that can readily be labeled with a radiolabel, such as Gd$^{3+}$ and $^{64}$Cu, resulting in Gd$^{3+}$-DOTA and $^{64}$Cu-DOTA respectively, attached to the quantum dot (nanoparticle). Optical properties of the cores (luminescence or fluorescence emission or plasmon frequency) are not affected by the addition of a silica shell or the presence of chelated paramagnetic ions. Other suitable chelates are known to those of skill in the art, for example, 1,4,7-triazacyclononane-N,N',N"-triacetic acid (NOTA) derivatives being among the most well-known (see, e.g., Lee et al. (1997) Nucl Med Biol. 24:225-23019).

In some embodiments the linking agent is a heterobifunctional crosslinker comprising two different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In some embodiments, an affinity agent (also referred to as a specific binding pair), e.g., agents that specifically binds to a ligand, is the linking agent. For instance, a first linking agent is bound to the semiconductor nanocrystal (nanoparticle) and a second linking agent is bound to a reporter, targeting entity, imaging or therapeutic agent. Affinity agents include receptor-ligand pairs, antibody-antigen pairs and other binding partners such as streptavidin/avidin and biotin. In one illustrative embodiment, the first linking agent is streptavidin or avidin and the second linking agent is biotin. the streptavidin or avidin is bound to the nanoparticle and a biotinylated agent (e.g., biotinylated imaging agent, biotinylated therapeutic, biotinylated antibody, etc.) is conjugated to the nanoparticle via streptavidin/avidin-biotin linkage. In some embodiments, other biotinylated radiolabel, peptides, proteins, antibodies, dyes, probes and other small molecules are attached to the streptavidin or avidin, and thus the nanoparticle.

In another embodiment, pendent functionalized linkers such as natural or modified polysaccharides as well as natural and modified nucleic or amino acids can be useful.

E. Polymer Matrix

The superparticle components, e.g., nanoparticles, reporter labels, and targeting entities, can be entrapped, immobilized, or encapsulated by physical or chemical means on or within the polymer matrix. Any suitable polymer may be used such as smart polymers or stimuli-responsive polymers, including hydrogels. As used herein, the term "entrap" and variations thereof is used interchangeably with "encapsulate" and is used to mean that the superparticle components can be immobilized within or on the constituents of the matrix. As used herein, "matrix" refers to essentially a three-dimensional environment which has the superparticle components immobilized therein for the purpose of measuring a detectable signal from analyte-superparticle interaction. The relationship between the constituents of the matrix and the nanoparticles/targeting entities/reporting labels, include, but are not limited to, covalent, ionic, and Van der Wals interactions and combinations thereof. The spatial relationship between the matrix and the superparticle components includes heterogeneous and homogeneous distribution within and or upon any or all of the matrix volume. The polymer matrix may be comprised of organic material, inorganic material, glass, metal, plastic, or combinations thereof.

The polymer matrix can be in any desirable form or shape including nanoparticle or microparticle providing it permits permeability to analyze. The polymer matrix additionally prevents leaching of the superparticle components from the sensor and allows for diffusion of analytes to the sensor. The polymer matrix permits light from optical sources or any other interrogating signals to or from the reporter group to pass through the sensor. When used in an in vivo application, the biosensor will be exposed to a substantially physiological range of analyte and determination or detection of a change in analyte concentration would be desired whereas the determination or detection includes continuous, programmed, and episodic detection means.

The polymer matrix may be prepared from biocompatible materials or incorporates materials capable of minimizing adverse reactions with the body. Adverse reactions for implants include inflammation, protein fouling, tissue necrosis, immune response and leaching of toxic materials. Such materials or treatments are well known and practiced in the art, for example as taught by Quinn, C. P.; Pathak, C. P.; Heller, A.; Hubbell, J. A. Biomaterials 1995, 16(5), 389-396, and Quinn, C. A. P.; Connor, R. E.; Heller, A. Biomaterials 1997, 18(24), 1665-1670.

In one embodiment, hydrogels as polymers are useful. As used herein, the term "hydrogel" is used to indicate a water-insoluble, water-containing polymer networks. Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are preferred. Synthesis and biomedical and pharmaceutical applications of hydrogels have been described by a number of researchers. (See, e.g. "Biosensors Fundamentals and Applications", edited by A. D. F. Turner, I. Karube and G. S. Wilson; published from Oxford University Press, in 1988). An exemplary hydrogel matrix derived from a water-soluble, UV crosslinkable polymer comprises poly(vinyl alcohol),N-methyl-4(4'-formylstyryl) pyridinium methosulphate acetal (CAS Reg. No. [107845-59-0]) available from PolyScience Warrington, Pa. In one embodiment, the selection of a suitable polymer such as a hydrogel should be such that the polymerization or gelling reaction of the matrix precursor would not adversely affect the activity of nanoparticle, the targeting entity, and/or reporter labels.

The polymers that are to be used in the hydrogel matrices may be functionalized. That is, the polymers or monomers comprising the polymers can possess reactive groups such that the hydrogel matrices are amenable to chemical reactions, e.g., covalent attachment. As used herein and throughout, a "reactive group" is a chemical group that can chemically react with a second group. The reactive group of the polymer or monomers comprising the polymer may itself be an entire chemical entity or it may be a portion of an entire chemical entity, including, but not limited to, single atoms or ions. Further, the second group with which the reactive group is capable of reacting can be the same or different from the reactive group of the polymer or monomers comprising the polymers. Examples of reactive groups include, but are not limited to, halogens, amines, amides, aldehydes, acrylates, vinyls, hydroxyls, thiols, and carboxyls. In one embodiment, the polymers or monomers comprising the polymers of the hydrogel should be functionalized with carboxylic acid, sulfate, hydroxy or amine groups. In another embodiment of the present invention, the polymers or monomers comprising the polymers of the hydrogel are functionalized with one or more acrylate groups. In one particular embodiment, the acrylate functional groups are terminal groups. The reactive groups of the polymers or monomers comprising the polymers of the matrix may be reactive with any component of the matrix portion of the biosensor, such as, but not limited to, another polymer or monomer within the matrix, a binding protein, an additive, the targeting entities, the reporter labels, linkers, and nanoparticles.

Suitable polymers which may be used in the present invention include, but are not limited to, one or more of the polymers selected from the group consisting of poly(vinyl alcohol), polyacrylamide, poly (N-vinyl pyrolidone), poly (ethylene oxide) (PEO), hydrolysed polyacrylonitrile, polyacrylic acid, polymethacrylic acid, poly(hydroxyethyl methacrylate), polyurethane polyethylene amine, poly(ethylene glycol) (PEG), cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. The polymers of the hydrogel matrix may also comprise polymers of two or more distinct monomers. Monomers used to create copolymers for use in the matrices include, but are not limited to acrylate, methacrylate, methyl methacrylate, methacrylic acid, alkylacrylates, phenylacrylate, hydroxyalkylacrylates, hydroxyalkylmethacrylates, aminoalkylacrylates, aminoalkylmethacrylates, alkyl quaternary salts of aminoalkylacrylamides, alkyl quaternary salts of aminoalkylmethacrylamides, and combinations thereof. Polymer components of the matrix may, of course, include blends of other polymers.

In one embodiment, the hydrogel is comprised of poly (ethylene glycol) dimethacrylate (PEGDMA). PEGDMA is commercially available in a variety of molecular weights. For example. PEGDMA is available from at least Aldrich Chemical Co. (Milwaukee, Wis. USA) and from Polysciences, Inc. (Warrington, Pa., USA) and can be synthesized in an assortment of molecular weights. In one embodiment, the molecular weight of PEGDMA used in the hydrogels of the present invention is from about 400 to about 4000. In a more specific embodiment, the molecular weight of the PEGDMA in the hydrogels is about 1000.

In another embodiment, the hydrogels comprise PEGDMA and at least one acrylate. As used herein, the term acrylate is well understood in the art. Specifically, acrylates are compounds, including but not limited to, polymers, comprising the acrylic group (HC2=CH—C(=O). Examples of acrylates include, but are not limited to, acrylic acid, ethyl acrylate, methacrylic acid, methyl methacrylic acid and acrylamides. In another specific embodiment, the hydrogels comprise more than one acrylate. In a more specific embodiment, the hydrogels comprise a mixture of methacrylate and methyl methacrylate.

The polymers used in the hydrogel matrices can be modified to contain nucleophilic or electrophilic groups. Indeed, the polymers used in the present invention may further comprise polyfunctional small molecules that do not contain repeating monomer units but are polyfunctional, i.e., containing two or more nucleophilic or electrophilic functional groups. These polyfunctional groups may readily be incorporated into conventional polymers by multiple covalent bond-forming reactions. For example, PEG can be modified to contain one or more amino groups to provide a nucleophilic group. Examples of other polymers that contain one or more nucleophilic groups include, but are not limited to, polyamines such as ethylenediamine, tetramethylenediamine, pentamethylenediamine, hexamethylenediamine, bis-(2-hydroxyethyl) amine, bis-(2-aminoethyl)amine, and tris-(2-aminoethyl)amine. Examples of electrophilic groups include but are not limited to, succinimide esters, epoxides, hydroxybenzotriazole esters oxycarbonylimidazoles, nitrophenyl carbonates, tresylates, mesylates, tosylates, carboxylates, and isocyanates. In one embodiment, the composition comprises a bis-amine-terminated poly(ethylene glycol). The polymer can assume any suitable structure. In one embodiment, the polymers can be linear. In some embodiments, the polymer can be star-shaped such as a multi-armed PEG structures.

In other embodiments, the polymers can include sacrificial components such as sugar crystals, salt crystals, surfactants, excipients, as well as inhibitors. The sacrificial components dissolve in the present of water or aqueous solution, generating pores in the polymer matrix to assist in target analyte diffusion into the super particle. In some embodiments, singlet oxygen scavengers, chemically reactive molecules and photoisomerizable chemical entities such as diazo- or dithiene-containing molecules can be included in the polymer matrix through mixing or conjugation.

The polymers should be capable of crosslinking, either physically or chemically, to form a hydrogel. Physical crosslinking includes, but is not limited to, such nonchemical processes as radiation treatment such as electron beams, gamma rays, x-rays, ultraviolet light, heat, anionic and cationic treatments. The crosslinking of the polymers may also comprise chemical crosslinking, such as covalent crosslinking. For example, a chemical crosslinking system may include, but is not limited to, the use of enzymes, which is well-known in the art. Another example of the chemical covalent crosslinking comprises the use of peroxide. Chemical crosslinking may occur when a crosslinking reagent reacts with at least two portions of a polymer to create a three-dimensional network. Covalent crosslinking may also occur when multifunctional monomers are used during the crosslinking process. For example, an acrylate monomer may be polymerized with a bifunctional acrylate monomer to form a crosslinked polymer. Any crosslinking reagent will be suitable for the present invention, provided the crosslinking reagent will at least partially dissolve in water or an organic solvent and can form the crosslinked polymer. For example, if the polymer is an amine-terminated PEG, the crosslinking reagent should be capable of reacting with the PEG-amine groups and be substantially soluble in water. In another example, (hydroxyethyl methacrylate) and methacrylic acid monomers can be polymerized with poly(ethylene glycol)-bis-alkylacrylate crosslinking agent in water or in dimethylformide to form polymeric hydrogels. The crosslinking reaction should be non-destructive to the superparticle components including the targeting entities, the reporter labels, and nanoparticles.

If the polymers to be crosslinked are functionalized with nucleophilic groups, such as amines (primary, secondary and tertiary), thiols, thioethers, esters, nitrites, and the like, the crosslinking reagent can be a molecule containing an electrophilic group. Examples of electrophilic groups have been described herein. Likewise, if polymers to be crosslinked are functionalized with electrophilic groups, the crosslinking reagent can be a molecule containing a nucleophilic group. It is understood that one skilled in the art can exchange the nucleophilic and electrophilic functional groups as described above without deviating from the scope of the present embodiment. It is also understood that the binding molecule can provide the requisite nucleophilic and electrophilic functional groups. For example, where the binding molecule is a protein, the nucleophilic and electrophilic functional groups may be present as naturally occurring amino acids in the protein, or may be introduced to the protein using chemical techniques described herein. Other general methods for preparing or crosslinking polymers to form hydrogel matrices are well known in the art. For example, Ghandehari H., et al., J. Macromol. Chem. Phys. 197: 965 (1996); and Ishihara K, et al., Polymer J., 16: 625 (1984), all of which are hereby incorporated by reference, report the formation of hydrogels. Hydrogel matrix can be applied to each sensor tip, e.g. a needle, and cured under a Hg lamp, with wavelength of >360 nm, for about 15 seconds.

In one embodiment of the present invention, one or more of the superparticle components can be covalently attached to and entrapped within a hydrogel. The covalent attachment of the superparticle component(s) to the hydrogel should not interfere with or prevent the binding of the target entities to the target ligand and subsequent detection of the binding event. In some embodiments, the covalent attachment of the superparticle component(s) to the hydrogel should be resistant to degradation. In one embodiment, the functional group in a polymer or other component of the hydrogel serves to couple the superparticle component(s) to the hydrogel. The coupling of the superparticle component(s) to the hydrogel can be accomplished in any number of ways. For example, coupling reactions between the hydrogel and binding molecule include, but are not limited to, diazonium coupling, isothiocyano coupling, hydrazide coupling, amide formation, disulfide coupling, maleic anhydride coupling, thiolactone coupling, and dichlotriazine coupling. These coupling reactions between two functional groups are well documented, and are considered well known to those skilled in the art. For example, an amino functional group in an targeting entity can be covalently coupled to a carboxyl functional group of one or more components of a hydrogel using coupling agents such as 1-ethyl-3-(3-dimethylaminopropyl) carbodiimide hydrochloride (EDC) or dicyclohexylcarbodiimide (DCC). It is understood that the amino and carboxyl functional groups of the binding molecule and one or more components of the hydrogel as described above can be transposed without deviating from the scope of the embodiment.

In another embodiment, the superparticle component(s) may be bound encapsulated non-covalently within polymer matrix or scaffold by any suitable means that allows analyte-induced conformational change of the targeting entity, e.g., aptamer, retension of the superparticle component(s) within the polymer to prevent loss or leaching of the superparticle component(s), and to provide a stable, continuous and reversible sensor response to changing concentrations of the target analyte of interest. For instance, well-established processes for enzyme immobilization in hydrogels may be used.

F. Method of Making Composite Particles

The superparticles can be made by any suitable process including, without limitation, casting, membrane extrusion, extrusion/electrospinning, microcontact printing, template assisted assembly, thin-film stretching, block-co-polymer self-assembly, micro-molding, and continuous processes such as roll-to-roll manufacturing or continuous flow reactors. In one embodiment, superparticles can be prepared by a casting method that enables the independent tuning of various parameters of the superparticles such as geometry, size, mechanical stiffness of the matrix material, and surface chemistry. Additionally, the casting method allows for high nanoparticle loading in the superparticle as well as spatially confining the nanoparticles for specific interactions such as FRET interactions. Furthermore, if the nanoparticles are made of a different modulus than the polymer matrix, e.g, hydrogel matrix, the high nanoparticle loading can also allow for modulation of the superparticle modulus. In one embodiment, the casting method includes the steps of (a) casting a solution of nanoparticles at least one type, reporter labels at least one type, targeting entities at least one type and a matrix precursor into a mold, the mold including a plurality of nanowells; (b) exposing the cast solution to a curing stimulus to form the superparticles; and (c) recovering the superparticles from the mold. In some embodiments, the reporter label, the targeting entity, or both are associated with the nanoparticles.

In another embodiment, the casting method includes the steps of (a) casting a solution of nanoparticles at least one type, reporter labels at least one type, targeting entities, and matrix precursors into a mold, the mold including a plurality of nanowells; (b) thermally annealing the nanoparticles in the cast solution in the wells; (c) exposing the thermally annealed cast solution to a curing stimulus to form the superparticles; and (d) recovering the superparticles from the mold. In some embodiments, the reporter label, the targeting entity, or both are associated with the nanoparticles.

The superparticles can be formed in any suitable shape in nanoscale such as nanospheres, nanorods, nanodisks, nanoplates and microscale such as pyramids, spheres, disks, rodes, cubes, sheets, and cones. For nanoscale size, the superparticles can range from 50 nm to 100 nm; from 100 nm to 500 nm; and from 500 nm to 999 nm. For microscale size, the superparticles can range from 1 microns to 10 microns, from 10 microns to 100 microns, and from 100 microns to 1000 microns, Molds having a plurality of individual nanowells in any suitable shape and size and a low surface energy structure can be useful to prepare superparticles and to ensure superparticle release from the molds. The material forming the molds can be non-wetting and non-swelling to both organic and inorganic materials. Generally, the dimensions of the nanowells in the molds can range from 50 nm height, 50 nm length, and 50 nm depth to 500 nm height, 500 nm length, and 500 nm depth.

The molds for preparing superparticles are commercially available from sources such as Micro Engineering Solutions (Charleston, City, Mass., USA). Alternatively, the molds can be manufactured using conventional techniques.

In one embodiment, the molds having nanowells can be manufactured by a coated master template method. The method involves creating and transferring a desired mold pattern from a photoresist prepared from SPR220-7, AZ5214e, maN-2403 or electron beam resist prepared from PMMA, XR-1541, ZEP520A. The surface of the molds can be treated by etching, e.g., by anisotropic etching via wet (e.g., KOH) or dry (e.g. SF6 and O2 or SF6+C4F8) processes. The sidewall slope angle of each nano- or micro-mold can be controlled using a non-undercutting etching process to facilitate mold release. The sidewalls and trench bottom of each nano- or micro-mold can be roughened by any suitable means. Thereafter, the roughened sidewalls of the individual nano- or micro-molds can be coated with a mold-release layer having a low surface energy. Any suitable coating layer may be applied either immediately prior to casting as a temporary layer using. The coating layer may also be a permanent layer using, for instance, parylene-C, Paralyne-D via CVD, CHF3 plasma, or TMCS/other silanes.

In another embodiment, the molds can be manufactured by an inverted template method. An inverted copy of a master mold template can be prepared via lithography and etching using the processes described above. The inverted template can then be used to cast a master template in low-energy material such as PFPE or PTFE.

In a further embodiment, the molds can be manufactured by direct fabrication in bulk low-energy material such as PTFE by depositing a hardmask (e.g., metal, Al2O3 or SiO2) via magnetron sputtering. The hardmask can be patterned via electron-beam lithography and then wet or dry etched. The mask pattern can then be transferred into mold material and followed by anisotropic dry etching (AR/O2 ion milling) of the mold material.

As shown in FIG. 1(a), the nanoparticles and liquid polymer matrix precursors are then combined and the resulting solution 120 is introduced in the nanowells 110 in the mold 100. In one embodiment, the amount of nanoparticles contained per volume of solution can ranges from 10,000 nanoparticles/mL to 10,000,000 nanoparticles/mL, generally 100,000 nanoparticles/mL to 8,000,000 nanoparticles/mL. In other embodiments, the amount of nanoparticles in the solution can range from 0.1% to 70% (w/w), generally 1% to 50% (w/w). The liquid polymer matrix precursors can be UV curable (e.g., PEGDA), temperature curable (e.g., Matrigel®, n-isopropyl acrylamide (NIPAAm), or pH curable. Any suitable technique may be used to drive or cast the solution into the nanowells of the mold. In one embodiment, the solution and mold can be centrifuged at a suitable speed, e.g., 4000 xg. In another embodiment, the solution can be introduced into a vacuum chamber including the mold. As shown in FIG. 1(a), once the solution of nanoparticles and liquid polymer matrix precursors are cast into the nanowells of mold, the solution is optionally thermally annealed 130 and then exposed to a suitable curing stimulus until the superparticle 140 solidifies. If desired, the thermal annealing step may be skipped if not required, depending on the nanoparticles. For magnetic nanoparticles, thermal annealing can be useful in assisting with the alignment of magnetic dipoles and formation of supercrystalline structures. The thermal annealing can be performed in the presence of a permanent magnet if desired. Depending on the choice of matrix precursors, any suitable curing stimulus may be used. In some embodiments, the curing stimulus can be, for instance, room temperature if a Michael reaction is involved; 45 degrees Celsius for an epoxide-amine reaction; neutralizing pH is collagen is the matrix precursor; or UV light if acrylates are used.

Once the superparticles are cured, the superparticles 140 can be collected or harvested in any suitable manner. In one embodiment, the superparticles are collected using a high surface energy film (e.g., PVA, polyvinylpyrrolidone (PVP), and polysaccharides). In another embodiment, the high surface energy film can have a backing such as flexible polymer backing such as plasticized polyurethane or PDMS. The film can then be dissolved in a suitable solvent (e.g., water for a PVP film) and the superparticles can then be harvested or collected by any suitable means. In one embodiment, the superparticles can be pelleted via centrifugation at a suitable speed (e.g., 12,000 rpm for 5-10 minutes, depending on particle size). In some embodiments involving superparticles having a sufficiently strong magnetization, such superparticles may be harvested through magnetic separation. In another embodiment, a mechanically flexible mold can be used so that removal of the superparticles can occur by twisting the mold.

Figure 1B:
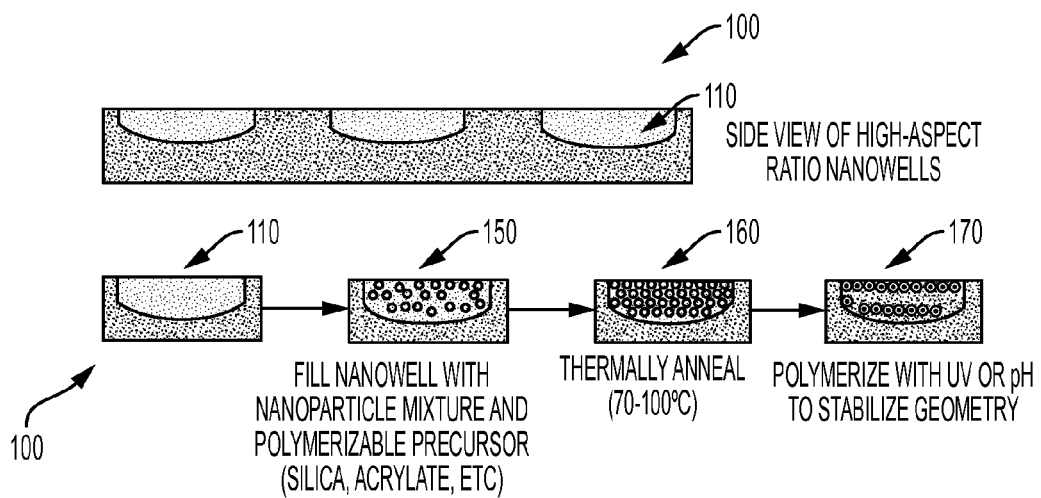

FIG. 1(b) shows another embodiment of a method of making superparticles 170 where two different types of nanoparticles are used in the solution 150, optionally thermally annealed 160, then exposed to a curing stimulus.

In one representative example, superparticles including magnetic nanoparticles is described. In this example, a solution of super paramagnetic iron oxide nanoparticles, a lipohilic silicate (tetraethyl orthosilicate (TEOS) or tetra-hexyl orthosilicate) in ethanol/THF solvent (e.g., 50-70% v/v superparametic iron oxide, balance TEOS) is casted into nanowells of a mold made of polytetrafluoroethylene (PTFE). The nanoparticles are thermally annealed while in the nanowells so that the nanoparticles can align their magnetic dipoles and form super crystalline structures. The nanoparticles are then exposed to NH3 or HCl vapors and/or elevated temperatures (e.g., up to 80 degrees Celsius) as the curing stimulus to set the silicate and form the superparticles. The superparticles are then removed from the molds using a PVA harvesting layer. The PVA layer is then dissolved in water and the superparticles are collected by centrifugation In another representative example, preparation of a superparticle including encapsulated sodium-responsive optode nanosensors comprising a matrix of polyvinyl chloride and bis(ethyl hexyl) sebacate (DOS) is described. The matrix of the superparticle can be a hydrophilic porous polymer or hydrogel. The design can be modular and other ionophores, organosoluble counterions, chromoionophores/reporters, plasticizers, polymers, and surfactants can be substituted. To prepare a sodium optode nanosensors, the following optode components are mixed, following the procedure described in, for instance, J. M. Dubach, D. I. Harjes, H. A. Clark, Nano letters, Vol. 7(6), 1827-1831, which is incorporated by reference in its entirety.

1.5 mg sodium ionophore X;

2 mg of sodium tetrakis [3,5-bis(trifluoromethyl phenyl] borate 0.5 mg of chromoionophore III;

0.1 mg of octadecylrhodamine B chloride;

30 mg PVC;

66 uL DOS 500 uL total tetrahydrofuran

The nanosensors are then sonicated in a surfactant-containing aqueous buffer or nanoprecipitated out by any suitable means. A solution of the optode nanosensors is then syringed filtered to isolate sub-100 nm diameter nanosensors. The nanosensors are then concentrated 100× using a centrifugal column (Amicon, 100 kDa filter). The nanosensors are then mixed with polymer matrix precursors to a volume ratio of 10 to 40%. The solution is then cast onto a mold containing wells having dimensions of 10 um×2 um×1 um with a volume of 20 um3 to produce superparticles of the same dimensions. The nanosensors are spherical, with a 120 nm mean diameter and volume of 0.00724 um3 per particle. For the following nanosphere volume fractions, the predicted number of nanosensors per superparticle is listed in Table 1 below.

TABLE 1

| Nanosensor density (v/v %) | Inactive component density (v/v %) | # nanosensors per superparticle |
|---|---|---|
| 70 | 30 | 193417 |
| 60 | 40 | 165786 |
| 50 | 50 | 138155 |
| 40 | 60 | 110524 |
| 30 | 70 | 82893 |
| 20 | 80 | 55262 |
| 10 | 90 | 27631 |
| 5 | 95 | 13815 |
| 1 | 99 | 2763 |

In another representative example, a superparticle including glucose nanoparticle sensors can be prepared. Measuring the electrochemical signal due to the enzymatic recognition of a specific analyte has produced several robust biosensor designs, most notably for glucose. In the glucose sensor, glucose oxidase processes glucose and consumes oxygen, which produces a measurable electrochemical change. However, many bioanalytes undergo multi-step, multi-enzyme processing. A biosensor may require two or more steps/enzymes before an enzyme produces a measurable change in the local environment. For example, gamma aminobutyric acid (GABA) is first processed by GABA transaminase, producing succinic semialdehyde and glutamate. Succinic semialdehyde is then processed by succinic semialdehyde dehydrogenase, which reduces the local pH. The components are mixed together in a hydrogen precursor solution and molded into superparticles, allowing the hydrogel matrix to set. Optionally, the enzyme and reporters can be conjugated to the matrix through orthogonal chemistries such as EDC/NHS and Michaels addition.

Figure 2A:
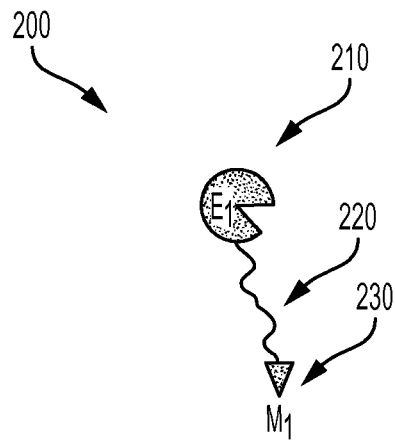
FIG. 2(a) illustrates an enzyme and modulator connected with a flexible linker; and 2(b) illustrates an a pair of enzymes and modulators connected with a flexible linker.
Figure 2B:
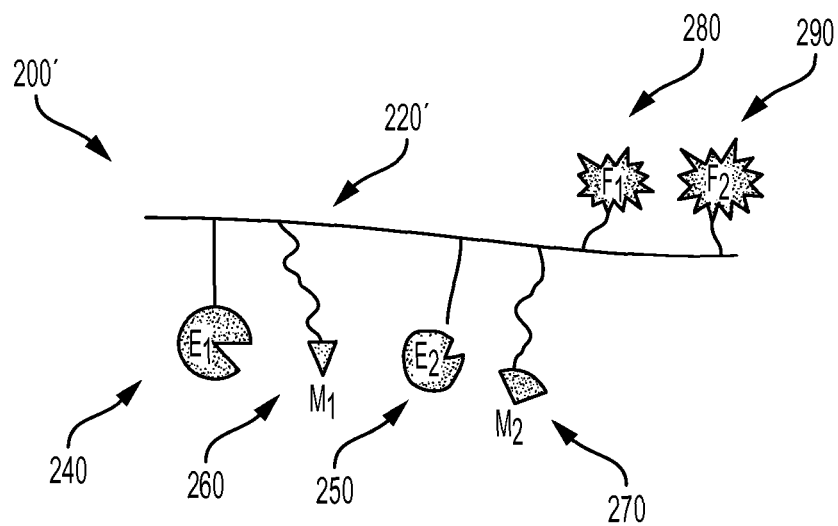

The component formulation will depend on the specific enzyme(s) used in the sensor design. An enzyme cascade may contain enzymes with much different rate constants and individual enzymes may be modulated by allosteric factors. In one embodiment for preparing such a sensor, a mixture of sensing components can be prepared. The enzymes can be conjugated to enzymatic modulators such as allosteric modulators or co-factors to activate or enhance the enzyme's activity. In one embodiment, a representative conjugate 200 including an enzyme E1 210 can be conjugated to a flexible linker 220 such as a heterobifunctional 10 kDa PEG which is then conjugated to modulator M1 230 as shown in FIG. 2(*a*). This ensures that at least one M1 molecule is near enzyme E1. In some embodiments, to increase the nanosensor's sensitivity, the relative composition fractions of subunits that are mixed together within the superparticle can be controlled.

In another embodiment, multi-enzyme and/or multi-modulator complexes can be wholly or partially assembled using functionalized polymers composed of DNA, natural and non-natural peptides, functionalized natural polymers, or pendent functionalized synthetic polymers as shown, for instance, in FIG. 2(*b*). FIG. 2(*b*) illustrates an enzyme cascade system 200' involving two enzymes E1 240 and E2 250 and a modulator for each enzyme 260 and 270, respectively, bound to a flexible linker 220'. A reporter labels such as fluorophores 280 and 290 can be conjugated to the flexible linker 220' (see FIG. 2(*b*)) or can be freely encapsulated with the superparticles. The reporter label can be environmentally-responsive fluorophores and reference fluorophores. Responsive fluorophores include, without limitation, O2-responsive porphyrins, pH indicators (e.g., derivatives of Nile red, fluorescein, and naphthalene), reduction/oxidation sensitive fluorophores (e.g., thiol containing fluorophores such as dyes, bipyridine dyes, phenanthrone-containing dyes and phenylamine-containing dyes), potentiometric indicators or temperature sensitive fluorophores. In one embodiment, a reporter label includes closely-spacing a fluorophore with no environmental sensitivity with a non-fluorescent quencher with environmental sensitivity. In some embodiments, to increase the nanosensor's sensitivity, the spacing between the fluorophores and targeting entities may be controlled through the relative stoichiometry of different pendent groups on a scaffold as shown in FIG. 2(*b*).

Figure 3:
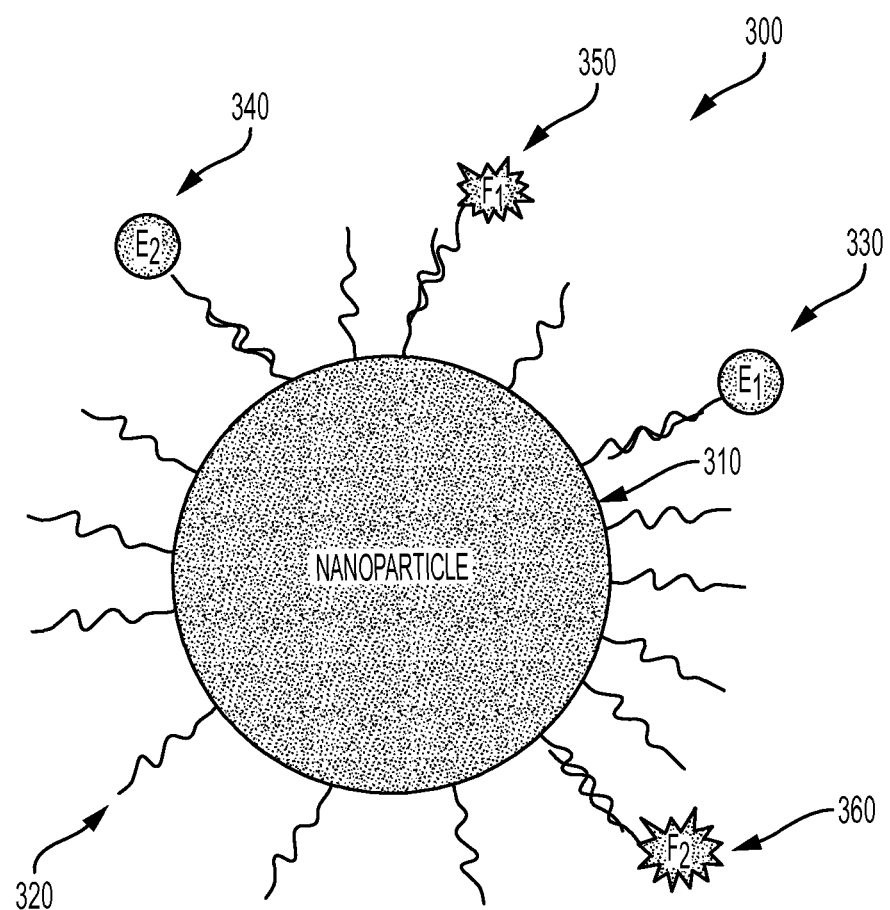
FIG. 3 illustrates a nanoparticle functionalized with several different single stranded DNA sequences (ssDNA). The nanosensor components are assembled around the nanoparticle core through base-pairing.

In another embodiment as shown in FIG. 3, the superparticle can include nanoparticle 300 that are functionalized on its surface 310 with a member of a specific binding pair such as complementary DNA strands, receptor-ligand, and/or biotin-strepavidin. The second member of the binding pair can be used to attach targeting entities, reporter labels, etc. onto the nanoparticles via binding interactions. In some embodiments, the superparticle includes a nanoparticle 300 onto which single stranded DNA 320 are attached. The single stranded DNA (ssDNA) 320 having different sequences can be attached to the nanoparticle by any suitable means including ligand exchange. For instance, on one end of the ssDNA can include a passivating group such as a thiol, carboxy, imidazole or amine that can bind to a surface of the nanoparticle or to a chemical group on the surface 310 of the nanoparticle 300. Compounds that include the passivating group either singly, bi- or as multi-dentate ligands can be used. The groups can be present singly in a c A second ssDNA that is complementary to at least one of the first ssDNA sequences can be conjugated to an enzyme such as E1 330 or E2 340, a modulator, reporter labels such as fluorophores F1 350 and F2 360, etc. as shown in FIG. 3. Under hybridization conditions, the second ssDNA conjugate can then hybridize to the complementary ssDNA bound to the nanoparticle. See FIG. 3. As shown in FIG. 3, a nanoparticle can be functionalized with several different ssDNA sequences, each complementary to a specific second ssDNA sequence conjugated to an enzyme (e.g., E1 or E2) or reporter label (F1 or F2). The nanosensor components are assembled around the nanoparticle core through base-pairing. The constituent nanosensors can then be encapsulated within the matrix of the superparticles. In some embodiments, some of the ssDNA attached to the surface of one nanoparticle can be complementary to other ssDNA attached to the surface of another nanoparticle. Under suitable hybridization conditions, the superparticles can be cured by the DNA base pairing between the nanoparticles. In other embodiments, the superparticles include nanoparticles that are functionalized with a member of a suitable binding pair such as biotin/avidin, streptavidin, or NeutrAvidin. One or more of the remaining components can be conjugated to the other member of the binding pair for subsequent binding to the nanoparticle.

In another embodiment, two or more types of nanoparticles can be included in the superparticle to impart desired properties. FIG. 3 illustrates casting a solution 150 of matrix precursors and two types of nanoparticles onto a wells 110 in a mold 100, thermally annealing the solution 160 and polymerizing the solution with a suitable curing stimulus, e.g, UV or heat, to produce a superparticle 170. In some embodiments, one or more types of nanoparticles can include magnetic nanoparticles, fluorescence nanoparticles, semiconductor nanoparticles, plasmonic nanoparticles, etc. In some embodiments, suitable magnetic nanoparticles can include, without limitation, $Fe_3O_4$, $Fe_2O_3$, FePt, FeCo, $Cd_2O_3$, $CoFe_2O_4$, and $MnFe_2O_4$. These particles can be paramagnetic or ferromagnetic. In some embodiments, the ferromagnetism can be induced by allowing constituent paramagnetic nanoparticles to assemble into supercrystalline lattice by heating at a suitable temperature, e.g., 80 to 200 degrees Celsius, and then cooling at a controlled rate, e.g., 1-5 degrees Celsius per hour.

In other embodiments, one or more types of nanoparticles can be fluorescent nanoparticles such as fluorophore-embedded silica nanoparticles, fluorophore encapsulating micelles, and flourophore embedded liposomes; inorganic semiconductor nanocrystals; organic semiconductor nanoparticles; or upconverting nanocrystals such as lanthanide-doped nanocrystals made of upconverting media including $YF_4$, $YAl_5O_{12}$, YLiF, and others. These nanoparticles can provide dynamic or reference signals, functioning as a reporter label or as optical barcodes to label overlapping sensor signals.

In other embodiments, the one or more types of nanoparticles can be plasmonic nanoparticles such as gold or silver nanoparticles. These nanoparticles can be spherical or non-spherical. Spherical nanoparticles may take on different aggregate plasmonic properties due to close packing. In some embodiments, tight packing can be induced using bifunctional linkers to join the nanoparticles into an aggregate. The arrangement of these plasmonic particles as well as their shapes can alter the local optical field to enhance fluorescence from fluorophores with the optical field. Analyte recognition may induce a perturbation in the arrangement in the plasmonic nanoparticles, thus producing a change in the detectable optical signal.

II. Diagnostic System Overview

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include ions such as sodium potassium, calcium, and chloride, enzymes, hormones, proteins, drug metabolites, tumor cells, tumor markers or other molecules.

In an example embodiment, the system obtains at least some of the health-related information by detecting the binding or interaction of a clinically-relevant analyte to or with materials such as superparticles, introduced into a lumen of the subsurface vasculature that have been functionalized with an targeting entity that has a specific affinity to bind to or interact with the specific analyte such as glucose. The term "binding" is understood in its broadest sense to also include a detectable interaction between the clinically relevant analyte and the superparticles. The superparticles can be introduced into the person's blood stream by injection, ingestion, inhalation, transdermally, or in some other manner.

The superparticles can be functionalized by covalently or otherwise attaching or associating a targeting entity that specifically binds, undergoes cell uptake or otherwise interacts with a particular clinically-relevant target analyte with a defined affinity to the target analyte. Other compounds or molecules, such reporter labels, e.g., fluorophores or autofluorescent or luminescent markers or non-optical contrast agents (e.g. acoustic impedance contrast, RF contrast and the like), which may assist in interrogating the nanoparticles in vivo, may also be attached to the nanoparticles.

The superparticles includes nanoparticles having a diameter that is generally equal to or less than about 200 micrometers. In some embodiments, the nanoparticles have a diameter on the order of about 10 nanometers to 1 micrometer. In further embodiments, small nanoparticles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, tryptophan, a virus, a phage, etc. Further, a particle may be of any shape, for example, spheres, rods, non-symmetrical shapes, etc.

In some examples, the superparticles include nanoparticles that can also be magnetic and can be formed from a paramagnetic, super-paramagnetic or ferromagnetic material or any other material that responds to a magnetic field. Alternatively, the nanoparticles may also be made of non-magnetic materials such as polystyrene. Where magnetic nanoparticles are used, the system may include a magnet that can direct into the portion of subsurface vasculature a magnetic field that is sufficient to manipulate aptamer-magnetic particle conjugates in a lumen of that portion of subsurface vasculature, for example, to collect or slow down in a certain area. However, measurements may be taken without localized "collection" of the superparticles. The system may be configured to activate the magnetic periodically, such as at certain times of the day (e.g., every hour).

The system may further include one or more data collection systems for interrogating, in a non-invasive manner, the superparticles present in a lumen of the subsurface vasculature in a particular local area. In one example, the system includes a detector configured to detect a response signal transmitted from a portion of subsurface vasculature. The response signal can include both an analyte response signal, which can be related to the interaction of the one or more target analytes with the superparticles, and a background noise signal. For example, the superparticles may include a chemiluminescent marker configured to produce a response signal in the form of luminescence radiation produced in response to a chemical reaction initiated, at least in part, to the binding of the target analyte to the particle.

In some examples, the system may also include an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal can be any kind of signal that is benign to the patient, such as electromagnetic, magnetic, optic, acoustic, thermal, mechanical, electric and results in a response signal that can be used to measure a physiological parameter or, more particularly, that can detect the binding or interaction of the clinically-relevant analyte to the superparticles. In one example, the interrogating signal is a radio frequency (RF) signal and the response signal is a magnetic resonance signal, such as nuclear magnetic resonance (NMR). In another example, where the superparticles include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector. In another example, where the superparticles include an electrically conductive material or a magnetically lossy material, the interrogation signal may be a time-varying magnetic field or a radio frequency (RF) electromagnetic signal, with sufficient signal power to rapidly heat the nanoparticles. The response signal may be an acoustic emission from the nanoparticles, caused by rapid thermal expansion of the nanoparticles, or caused by cavitation of the liquid medium in contact with the nanoparticles. As described above, in some cases, an interrogating signal may not be necessary to produce an analyte response signal.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to superparticles bound to or interacting with target analyte(s)—and an "unbound" particle signal—related to superparticles not bound to or interacting with target analyte(s). For example, in some measurement or characterization schemes, it may be useful to determine the percentage of superparticles introduced into the body that have bound to the target analyte. In such cases, the modulation source may be configured to modulate the analyte response signal differently than the unbound particle signal.

Data collected by the detector may be sent to a processor for analysis. The processor may be configured to non-invasively detect the one or more target analytes by differentiating the analyte response signal from the background noise signal based, at least in part, on the modulation. In some cases, the processor may further be configured to differentiate the analyte response signal from the unbound particle signal. Further, the processor may be configured to determine the concentration of a particular target analyte in the blood from, at least in part, the analyte response signal. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has not responded to chemotherapy when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a device. In one embodiment, the device is a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

III. Example Wearable Devices

In some examples, the wearable devices described herein obtain at least some of the health-related information by detecting the binding of a clinically-relevant analyte such as a tumor marker to the superparticles. The superparticles can be introduced into the person's blood stream by injection, ingestion, inhalation, transdermally, or in some other suitable manner.

Figure 4:
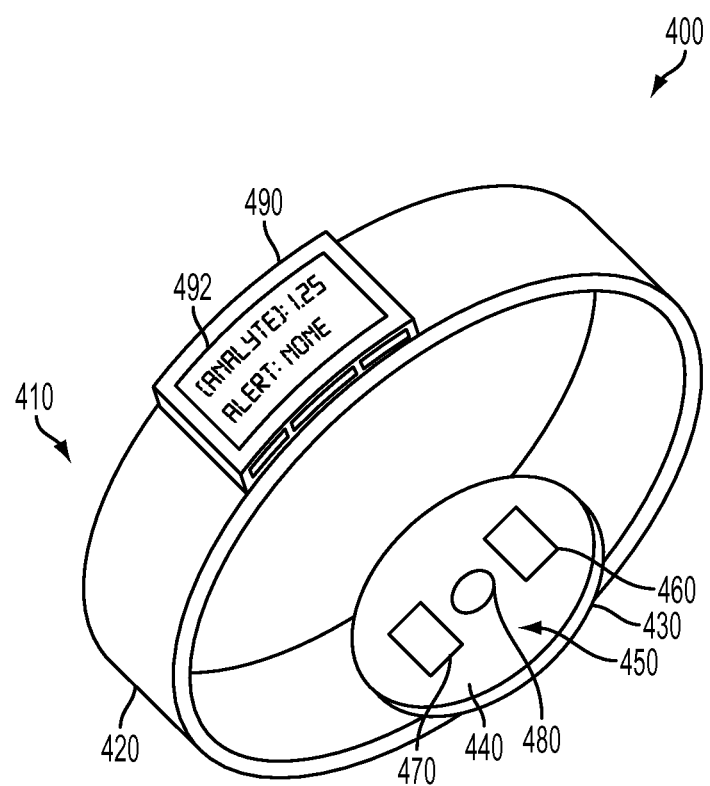
FIG. 4 is a perspective view of an example wearable device.

A wearable device 400 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A measurement platform 430 is disposed on the mount 410 such that it can be positioned on the body where subsurface vasculature is easily observable. An inner face 440 of the measurement platform is intended to be mounted facing to the body surface. The measurement platform 430 may house a data collection system 450, which may include at least one detector 460 for detecting at least one physiological parameter. The at least one physiological parameter could be any parameter that may relate to the health of the person wearing the wearable device. For example, the detector 460 could be configured to measure blood pressure, pulse rate, respiration rate, skin temperature, etc. At least one of the detectors 460 is configured to non-invasively measure one or more analytes in blood circulating in subsurface vasculature proximate to the wearable device. In a non-exhaustive list, detector 460 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 450 may be miniaturized so that the wearable device may be worn on the body without significantly interfering with the wearer's usual activities.

In some examples, the data collection system 450 further includes a signal source 470 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the superparticles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the nanoparticles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the superparticles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 400 may not include a signal source 470. For example, the superparticles include an autofluorescent or luminescent marker, such as a fluorophore, that will automatically emit a response signal indicative of the binding of the clinically-relevant analyte to the superparticles, without the need for an interrogating signal or other external stimulus. In some examples, the superparticles may include a chemiluminescent marker configured to produce a response signal in the form of luminescence radiation produced in response to a chemical reaction initiated, at least in part, to the binding of the target analyte to the particle.

A collection magnet 480 may also be included in the data collection system 450. In such embodiments, the superparticles may also be made of or be functionalized with magnetic materials, such as ferromagnetic, paramagnetic, super-paramagnetic, or any other material that responds to a magnetic field. The collection magnet 480 is configured to direct a magnetic field into the portion of subsurface vasculature that is sufficient to cause the magnetic superparticles to collect in a lumen of that portion of subsurface vasculature. The magnet may be an electromagnet that may be turned on during measurement periods and turned off when a measurement period is complete so as to allow the magnetic nanoparticles to disperse through the vasculature.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured physiological parameters, for instance, the concentrations of certain blood analytes being measured.

The wearable device may, in some cases, also include a modulation source. The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, nanoparticles, cells, molecules, blood components, bone and tissues, etc.

This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

The modulation source may apply a modulation, configured to modulate the response signal, to the portion of the body. Specifically, the modulation source may be configured to modulate the analyte response signal differently from a background signal. The background signal may include any signal transmitted from something other than what the system is monitoring, i.e., the target analyte(s). In some examples, the background signal may be generated by other molecules, cells, or nanoparticles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In some examples, the modulation source may be configured to modulate the analyte response signal (transmitted from bound nanoparticles) differently than the unbound particle signal (transmitted from nanoparticles that are not bound or otherwise interacting with the target analyte(s)), such that the analyte response signal may be differentiated from the unbound particle signal. Such differentiation may be used to determine the number or percentage of nanoparticles bound to or interacting with the target analyte(s), which may be used to determine a concentration of the target analyte(s) in the blood or other bodily fluid, to determine if and to what extent the nanoparticles are being cleared from the body, etc.

The modulation source may include any means for modulating the response signal. In some cases, the analyte response signal may be modulated differently than the background signal, and in other cases the analyte response signal may be modulated differently than the unbound particle signal, or both. For example, the modulation source may be configured to alter the spatial, optical magnetic, electric, acoustic, and/or physical properties of the bound nanoparticles. The modulation source may be a physical construct or it may be a signal or energy applied to the body, or a combination thereof. Accordingly, the modulation may include spatial, temporal, spectral, thermal, magnetic, optical, mechanical, electrical, acoustic, chemical, or electrochemical type of modulation or any combination thereof.

Figure 5A:
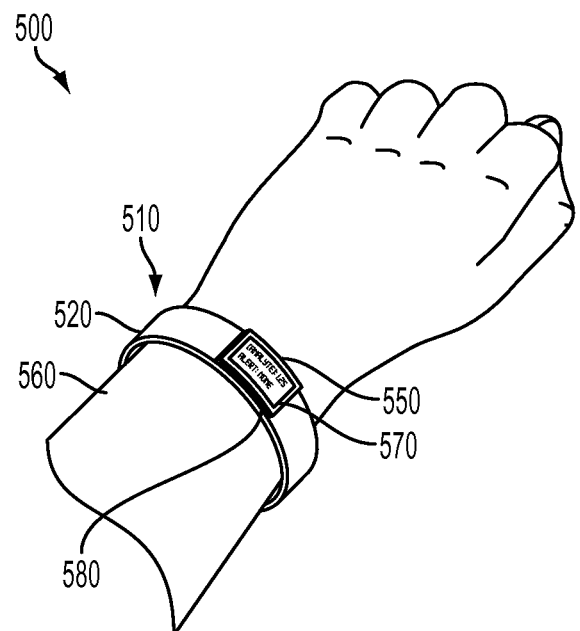
FIG. 5A is a perspective top view of an example wrist-mounted device, when mounted on a wearer's wrist.
Figure 5B:
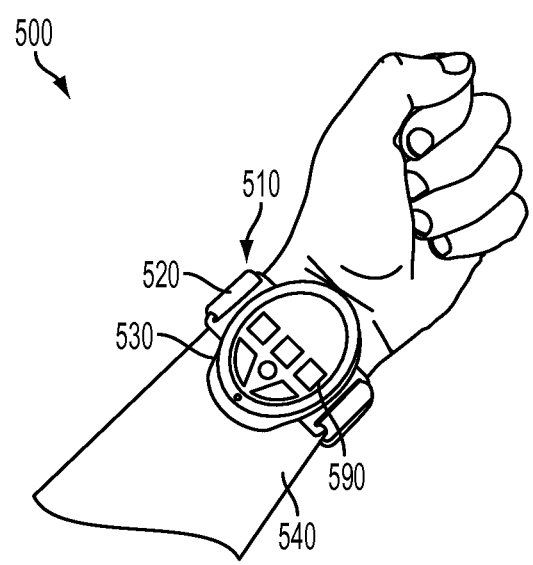
FIG. 5B is a perspective bottom view of an example wrist-mounted device shown in FIG. 2A, when mounted on a wearer's wrist.

In one example, the wearable device is provided as a wrist-mounted device, as shown in FIGS. 5A, 5B, 6A-6C, 7A, 8B, and 9. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a measurement platform 530 positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the measurement platform 530 may be located on the anterior side 540 of the wearer's wrist where the subsurface vasculature may be readily observable. However, other configurations are contemplated.

The display 570 may be configured to display a visual indication of the alert or recommendation and/or an indication of the measured physiological parameters, for instance, the concentrations of certain blood analytes being measured. Further, the user interface 550 may include one or more buttons 580 for accepting inputs from the wearer. For example, the buttons 580 may be configured to change the text or other information visible on the display 570. As shown in FIG. 5B, measurement platform 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 6A:
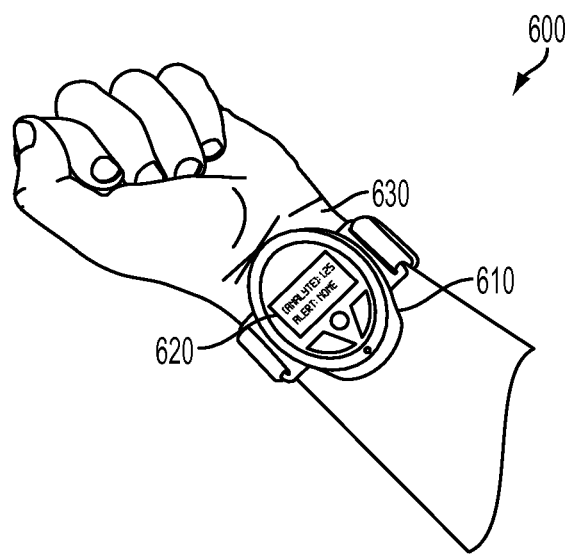
FIG. 6A is a perspective bottom view of an example wrist-mounted device, when mounted on a wearer's wrist.
Figure 6B:
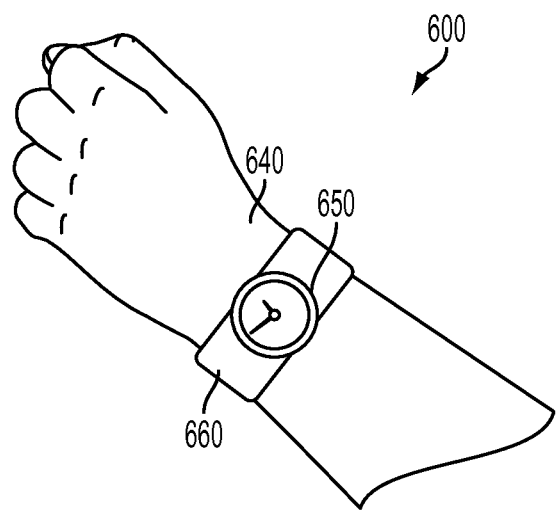
FIG. 6B is a perspective top view of an example wrist-mounted device shown in FIG. 6A, when mounted on a wearer's wrist.
Figure 6C:
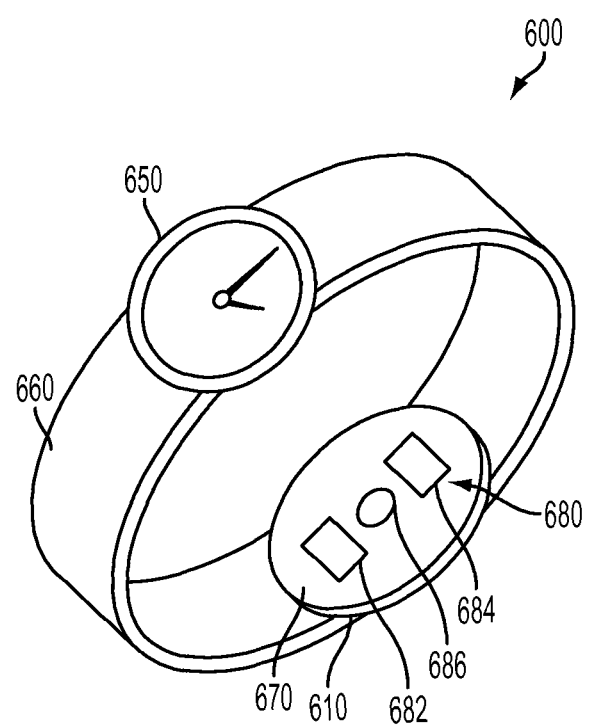
FIG. 6C is a perspective view of an example wrist-mounted device shown in FIGS. 6A and 6B.

In another example wrist-mounted device 600, shown in FIGS. 6A-6C, the measurement platform 610 and user interface 620 are both provided on the same side of the wearer's wrist, in particular, the anterior side 630 of the wrist. On the posterior side 640, a watch face 650 may be disposed on the strap 660. While an analog watch is depicted in FIG. 6B, one of ordinary skill in the art will recognize that any type of clock may be provided, such as a digital clock.

As can be seen in FIG. 6C, the inner face 670 of the measurement platform 610 is intended to be worn proximate to the wearer's body. A data collection system 680 housed on the measurement platform 610 may include a detector 682, a signal source 684 and a collection magnet 686. As described above, the signal source 684 and the collection magnet 686 may not be provided in all embodiments of the wearable device.

Figure 7A:
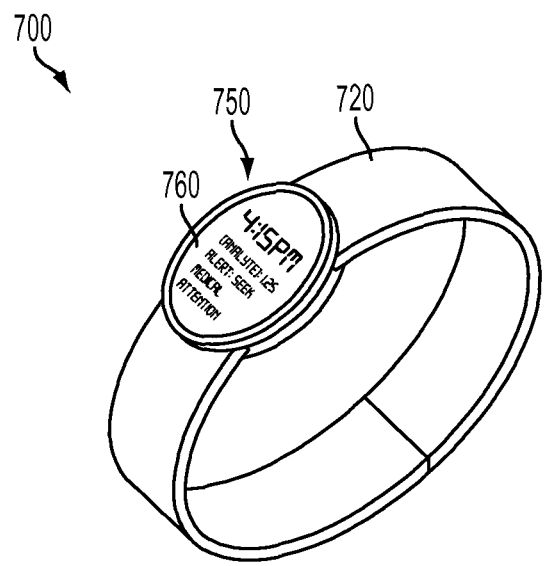
FIG. 7A is a perspective view of an example wrist-mounted device.
Figure 7B:
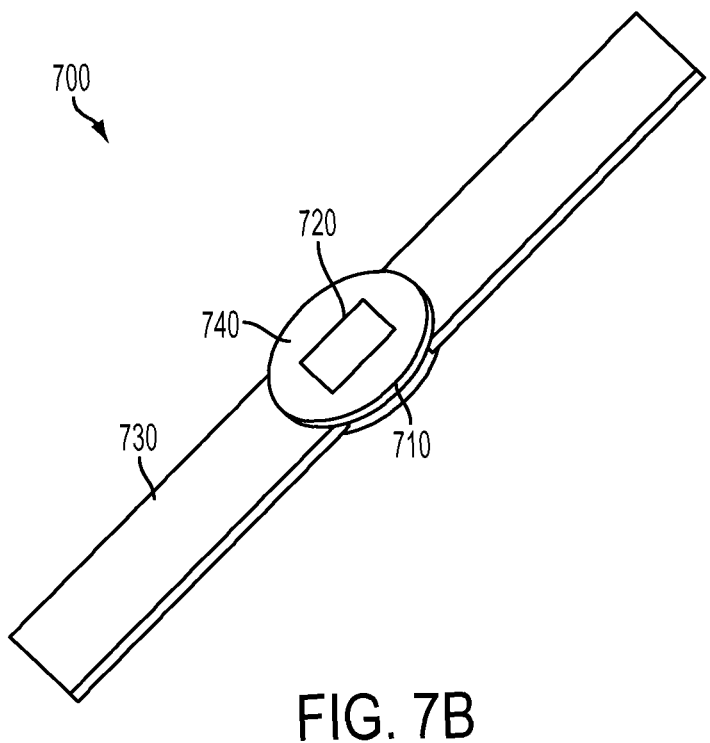
FIG. 7B is a perspective bottom view of an example wrist-mounted device shown in FIG. 7A.

In a further example shown in FIGS. 7A and 7B, a wrist mounted device 700 includes a measurement platform 710, which includes a data collection system 720, disposed on a strap 730. Inner face 740 of measurement platform may be positioned proximate to a body surface so that data collection system 720 may interrogate the subsurface vasculature of the wearer's wrist. A user interface 750 with a display 760 may be positioned facing outward from the measurement platform 710. As described above in connection with other embodiments, user interface 750 may be configured to display data collected from the data collection system 720, including the concentration of one or more measured analytes, and one or more alerts generated by a remote server or other remote computing device, or a processor located on the measurement platform. The user interface 720 may also be configured to display the time of day, date, or other information that may be relevant to the wearer.

Figure 8:
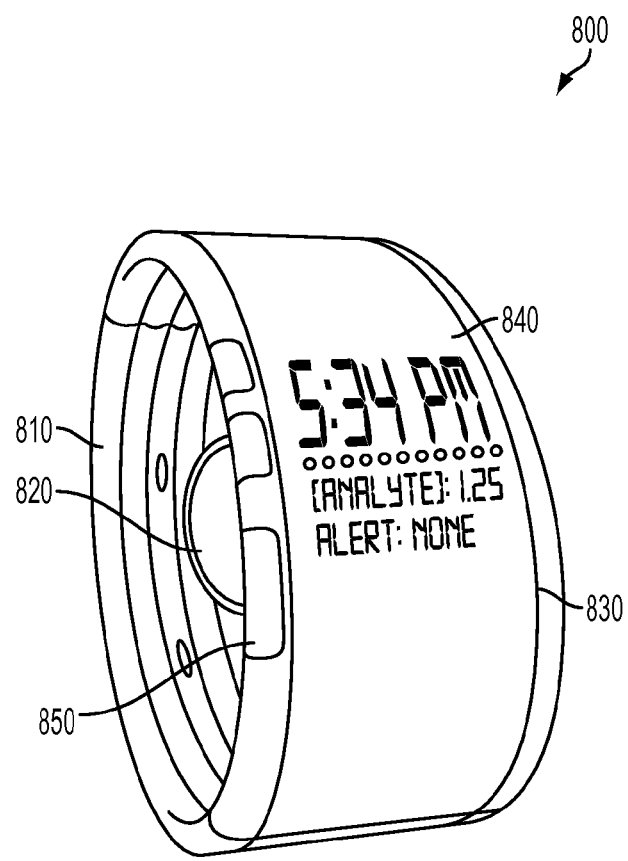
FIG. 8 is a perspective view of an example wrist-mounted device.
Figure 9:
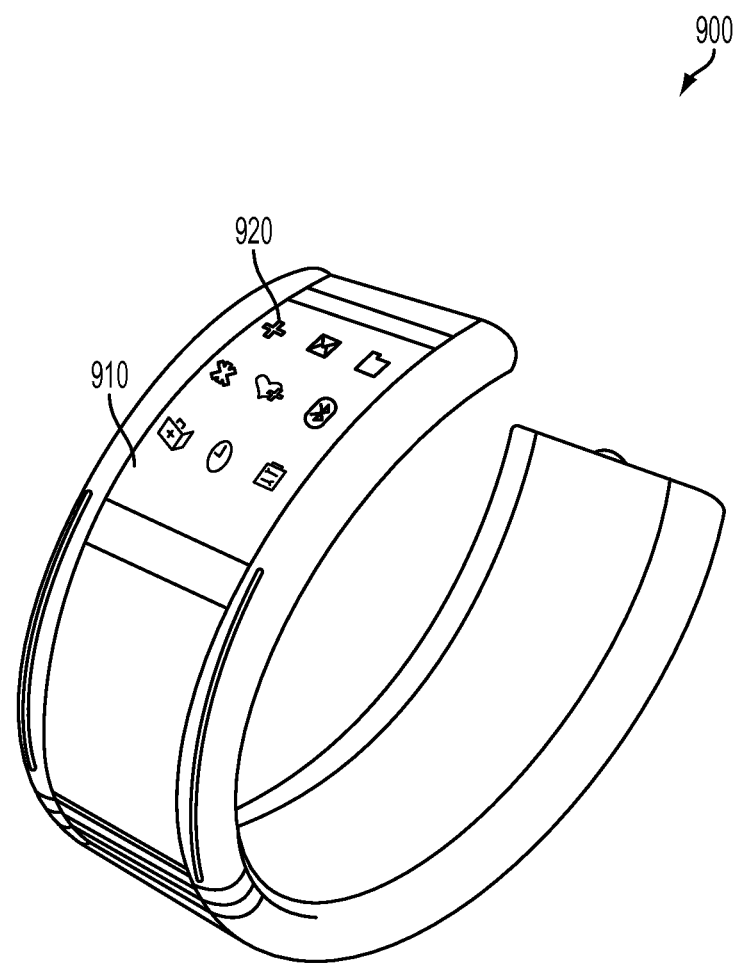
FIG. 9 is a perspective view of an example wrist-mounted device.

As shown in FIG. 8, in a further embodiment, wrist-mounted device 800 may be provided on a cuff 810. Similar to the previously discussed embodiments, device 800 includes a measurement platform 820 and a user interface 830, which may include a display 840 and one or more buttons 850. The display 840 may further be a touch-screen display configured to accept one or more input by the wearer. For example, as shown in FIG. 9, display 910 may be a touch-screen configured to display one or more virtual buttons 920 for accepting one or more inputs for controlling certain functions or aspects of the device 900, or inputs of information by the user, such as current health state.

Figure 10:
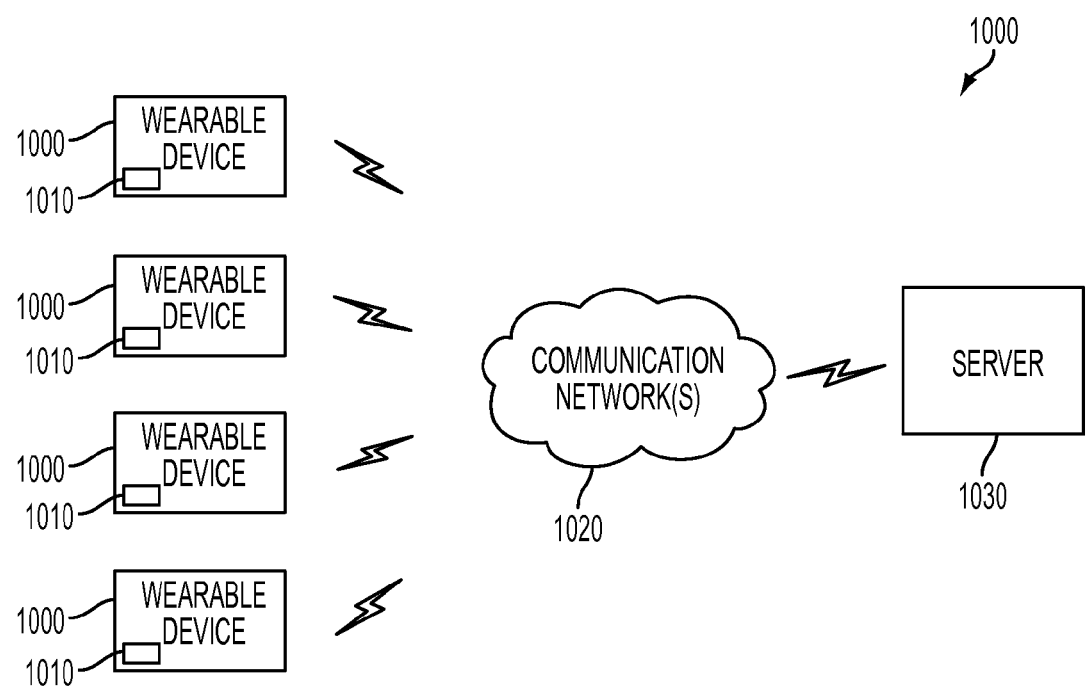
FIG. 10 is a block diagram of an example system that includes a plurality of wearable devices in communication with a server.

FIG. 10 is a simplified schematic of a system including one or more wearable devices 1000. The one or more wearable devices 1000 may be configured to transmit data via a communication interface 1010 over one or more communication networks 1020 to a remote server 1030. In one embodiment, the communication interface 1010 includes a wireless transceiver for sending and receiving communications to and from the server 1030. In further embodiments, the communication interface 1010 may include any means for the transfer of data, including both wired and wireless communications. For example, the communication interface may include a universal serial bus (USB) interface or a secure digital (SD) card interface. Communication networks 1020 may be any one of may be one of: a plain old telephone service (POTS) network, a cellular network, a fiber network and a data network. The server 1030 may include any type of remote computing device or remote cloud computing network. Further, communication network 1020 may include one or more intermediaries, including, for example wherein the wearable device 1000 transmits data to a mobile phone or other personal computing device, which in turn transmits the data to the server 1030.

In addition to receiving communications from the wearable device 1000, such as collected physiological parameter data and data regarding health state as input by the user, the server may also be configured to gather and/or receive either from the wearable device 1000 or from some other source, information regarding a wearer's overall medical history, environmental factors and geographical data. For example, a user account may be established on the server for every wearer that contains the wearer's medical history. Moreover, in some examples, the server 1030 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure tumor marker concentrations. If a wearer is prescribed a drug intended to treat cancer, but the server receives data from the wearable device indicating that the wearer's tumor marker concentration has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Example Electronics Platform for a Wearable Device

Figure 11:
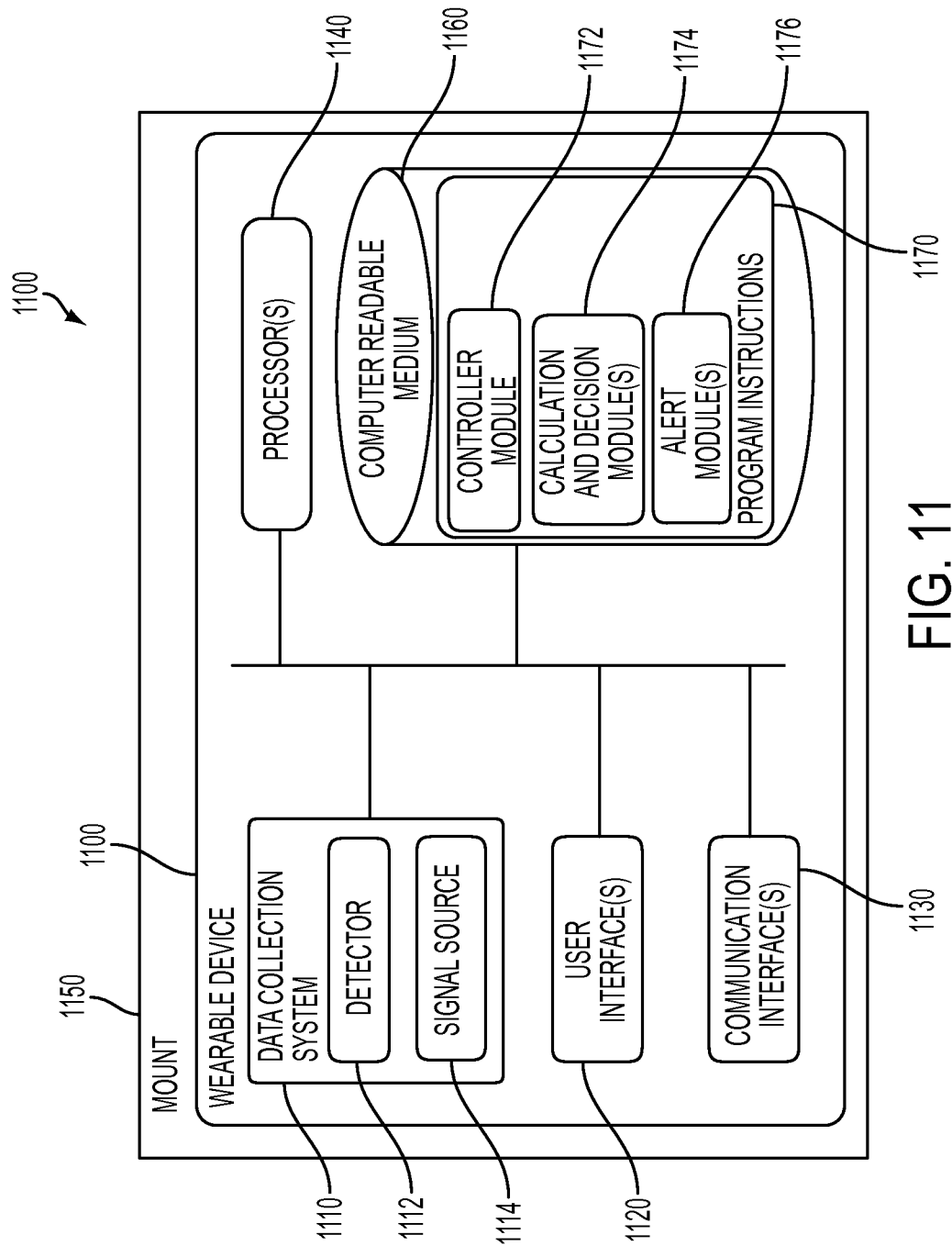
FIG. 11 is a functional block diagram of an example wearable device.

FIG. 11 is a simplified block diagram illustrating the components of a wearable device 1100, according to an example embodiment. Wearable device 800 may take the form of or be similar to one of the wrist-mounted devices 500, 600, 700, 800, 900, shown in FIGS. 5A-B, 6A-6C, 7A-7C, 8 and 9. However, wearable device 1100 may also take other forms, such as an ankle, waist, or chest-mounted device.

In particular, FIG. 11 shows an example of a wearable device 1100 having a data collection system 1110, a user interface 1120, communication platform 1130 for transmitting data to a server, and processor(s) 1140. The components of the wearable device 1100 may be disposed on a mount 1150 for mounting the device to an external body surface where a portion of subsurface vasculature is readily observable.

Processor 1140 may be a general-purpose processor or a special purpose processor (e.g., digital signal processors, application specific integrated circuits, etc.). The one or more processors 1140 can be configured to execute computer-readable program instructions 1170 that are stored in the computer readable medium 1160 and are executable to provide the functionality of a wearable device 1100 described herein.

The computer readable medium 1160 may include or take the form of one or more non-transitory, computer-readable storage media that can be read or accessed by at least one processor 1140. The one or more computer-readable storage media can include volatile and/or non-volatile storage components, such as optical, magnetic, organic or other memory or disc storage, which can be integrated in whole or in part with at least one of the one or more processors 1140. In some embodiments, the computer readable medium 1160 can be implemented using a single physical device (e.g., one optical, magnetic, organic or other memory or disc storage unit), while in other embodiments, the computer readable medium 1160 can be implemented using two or more physical devices.

Data collection system 1110 includes a detector 1112 and, in some embodiments, a signal source 1114. As described above, detector 1112 may include any detector capable of detecting at least one physiological parameter, which could include any parameters that may relate to the health of the person wearing the wearable device. For example, the detector 1112 could be configured to measure blood pressure, pulse rate, skin temperature, etc. At least one of the detectors 1112 is configured to non-invasively measure one or more analytes in blood circulating in subsurface vasculature proximate to the wearable device. In some examples, detector 1112 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 1110 further includes a signal source 1114 for transmitting an interrogating signal that can penetrate the wearer's skin into the portion of subsurface vasculature. In general, signal source 1114 will generate an interrogation signal that will produce a responsive signal that can be detected by one or more of the detectors 1112. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the superparticles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the nanoparticles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the superparticles include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 1170 stored on the computer readable medium 1160 may include instructions to perform or facilitate some or all of the device functionality described herein. For instance, in the illustrated embodiment, program instructions 1170 include a controller module 1172, calculation and decision module 1174 and an alert module 1176.

The controller module 1172 can include instructions for operating the data collection system 1110, for example, the detector 1112 and signal source 1114. For example, the controller 1172 may activate signal source 1114 and/or detector 1112 during each of the pre-set measurement periods. In particular, the controller module 1172 can include instructions for controlling the signal source 1114 to transmit an interrogating signal at preset measurement times and controlling the detector 1112 to receive data representative of response signals transmitted from the portion of subsurface vasculature in response to the interrogating signals transmitted at the preset measurement times.

The controller module 1172 can also include instructions for operating a user interface 1120. For example, controller module 1172 may include instructions for displaying data collected by the data collection system 1110 and analyzed by the calculation and decision module 1174, or for displaying one or more alerts generated by the alert module 1175. Further, controller module 1172 may include instructions to execute certain functions based on inputs accepted by the user interface 1120, such as inputs accepted by one or more buttons disposed on the user interface.

Communication platform 1130 may also be operated by instructions within the controller module 1172, such as instructions for sending and/or receiving information via a wireless antenna, which may be disposed on or in the wearable device 1100. The communication interface 1130 can optionally include one or more oscillators, mixers, frequency injectors, etc. to modulate and/or demodulate information on a carrier frequency to be transmitted and/or received by the antenna. In some examples, the wearable device 1100 is configured to indicate an output from the processor by modulating an impedance of the antenna in a manner that is perceivable by a remote server or other remote computing device.

Calculation and decision module 1172 may include instructions for receiving data from the data collection system 1110 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 1172 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 1172 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 1160 may further contain other data or information, such as medical and health history of the wearer of the device, that may be useful in determining whether a medical condition is indicated. Further, the computer readable medium 1160 may contain data corresponding to certain analyte baselines, above or below which a medical condition is indicated. The baselines may be pre-stored on the computer readable medium 1160, may be transmitted from a remote source, such as a remote server, or may be generated by the calculation and decision module 1174 itself. The calculation and decision module 1174 may include instructions for generating individual baselines for the wearer of the device based on data collected over a certain number of measurement periods. For example, the calculation and decision module 1174 may generate a baseline concentration of a target blood analyte for each of a plurality of measurement periods by averaging the analyte concentration at each of the measurement periods measured over the course of a few days, and store those baseline concentrations in the computer readable medium 1160 for later comparison. Baselines may also be generated by a remote server and transmitted to the wearable device 1100 via communication interface 1130. The calculation and decision module 1174 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 1174 that a medical condition is indicated, the alert module 1176 may generate an alert via the user interface 1120. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 12:
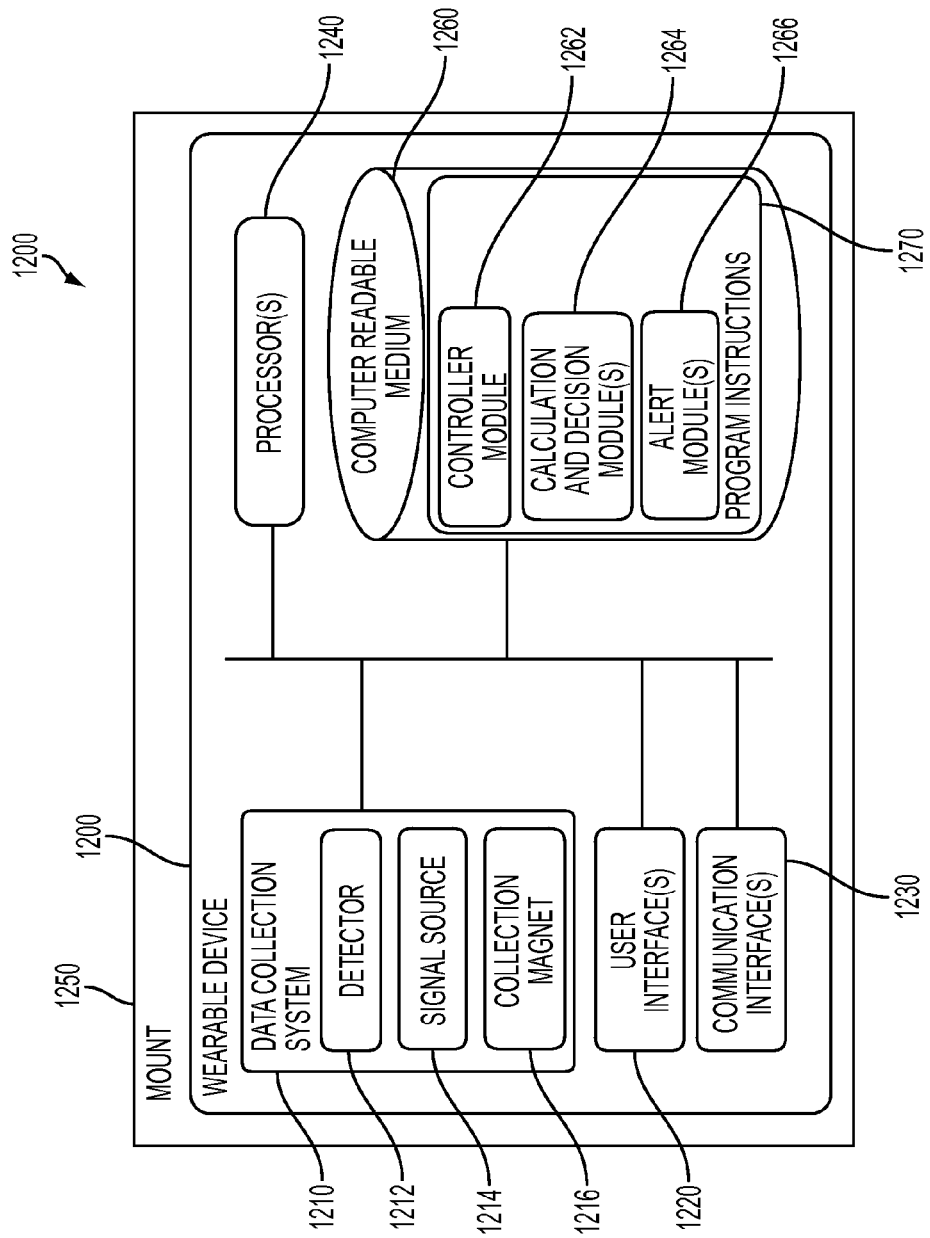
FIG. 12 is a functional block diagram of an example wearable device.

FIG. 12 is a simplified block diagram illustrating the components of a wearable device 1200, according to an example embodiment. Wearable device 1200 is the same as wearable device 1100 in all respects, except that the data collection system 1210 of wearable device 1200 further includes a collection magnet 1216. In this example, the collection magnet 1216 may be used to locally collect magnetic nanoparticles conjugates present in an area of subsurface vasculature proximate to the collection magnet 1216. As described above, collection magnet 1216 is configured to direct a magnetic field into a portion of subsurface vasculature sufficient to cause the magnetic nanoparticles conjugates to collect in a lumen of the portion of subsurface vasculature.

Wearable device 1200 includes a data collection system 1210, which includes a detector 1212, a signal source 1214 (if provided) and a collection magnet 1216, a user interface 1220, a communication interface 1230, a processor 1240 and a computer readable medium 1260 on which program instructions 1270 are stored. All of the components of wearable device 1200 may be provided on a mount 1250. In this example, the program instructions 1270 may include a controller module 1262, a calculation and decision module 1264 and an alert module 1266 which, similar to the example set forth in FIG. 11, include instructions to perform or facilitate some or all of the device functionality described herein. Controller module 1262 further includes instructions for operating collection magnet 1216. For example, controller module 1262 may include instructions for activating collection magnet during a measurement period, for a certain amount of time.

Figure 13:
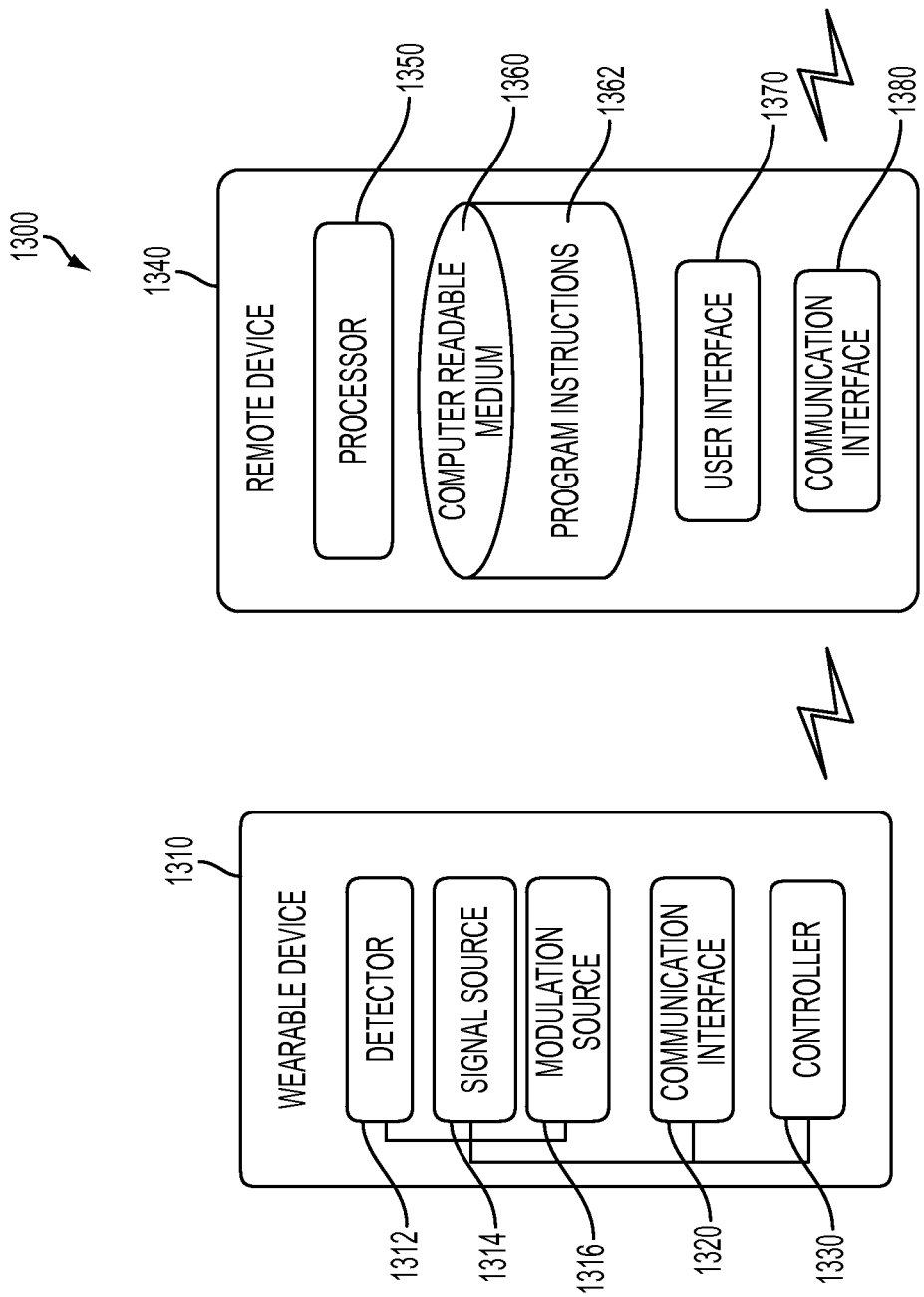
FIG. 13 is a functional block diagram of an example system including a wearable device and a remote device.

FIG. 13 is a simplified block diagram illustrating the components of an example system 1300, including a wearable device 1310. Wearable device 1310 may take the form of or be similar to one of the wrist-mounted devices 500, 600, 700, 800, or 900, shown in FIGS. 5A-B, 6A-6C, 7A-7C, 8, and 9. However, wearable device 1310 may also take other forms, such as an ankle, waist, ear, eye or chest-mounted device. Further, any of devices 500, 600, 700, 800, and 900 may be configured similar to or include any of the components of system 1300, including wearable device 1310.

In particular, FIG. 13 shows an example of a system 1300 including a wearable device 1310 having a detector 1312, in some examples, a signal source 1314, a modulation source 1316, and a communication interface 1320, controlled by a controller 1330. Communication interface 1320 may include an antenna. The components of the wearable device 1310 may be disposed on a mount (not shown) for mounting the device to an external body surface where a portion of subsurface vasculature is readily observable. System 1300 may further include a remote device 1340 in communication with the wearable device 1310, including a processor 1350, a computer readable medium 1360, a user interface 1370, and a communication interface 1380 for communicating with the wearable device 1310 and/or for transmitting data to a server or other remote computing device. While FIG. 13 depicts various components of system 1300 disposed on the wearable device 1310 or the remote device 1340, one of ordinary skill in the art would understand that different configurations and designs are possible, including where all of the components are provided on the wearable device.

Processor 1350 may be a general-purpose processor or a special purpose processor (e.g., digital signal processors, application specific integrated circuits, etc.) and can be configured to execute computer-readable program instructions 1362 that are stored in the computer readable medium 1360 and are executable to provide the functionality of a system 1300 as described herein. The computer readable medium 1360 may include or take the form of one or more non-transitory, computer-readable storage media that can be read or accessed by the processor 1350, and can include volatile and/or non-volatile storage components, such as optical, magnetic, organic or other memory or disc storage, which can be integrated in whole or in part with the processor 1350. The controller 1330 may be configured to operate one or more of the detector 1312, signal source 1314 and modulation source 1316. For example, the controller 1330 may activate the detector 1312, signal source 1314 and modulation source 1316 during each of the pre-set measurement periods.

The program instructions 1362 stored on the computer readable medium 1360 may include instructions to perform or facilitate some or all of the system functionality described herein. For instance, in the illustrated embodiment, program instructions 1362 may include instructions for controller 1330 to operate the detector 1312, signal source 1314 and modulation source 1316. Program instructions 1362 may further cause the processor 1350 to detect the one or more target analytes by differentiating the analyte response signal from the background signal based, at least in part, on a modulation applied by the modulation source 1316. In some cases, the processor may further be configured to differentiate the analyte response signal from the unbound particle signal. Further, the processor 1350 may be configured to determine the concentration of a particular target analyte in the blood from, at least in part, the analyte response signal. The detection and concentration data processed by the processor may be communicated to the patient, for example via the user interface 1370, transmitted to medical or clinical personnel, locally stored or transmitted to a remote server, the cloud, and/or any other system where the data may be stored or accessed at a later time. The program instructions 1362 may also include instructions for operating a user interface 1370, for example, instructions for displaying data transmitted from the wearable device 1310 and analyzed by the processor 1350, or for generating one or more alerts.

V. Illustrative Methods for Operation of a Wearable Device

Figure 14:
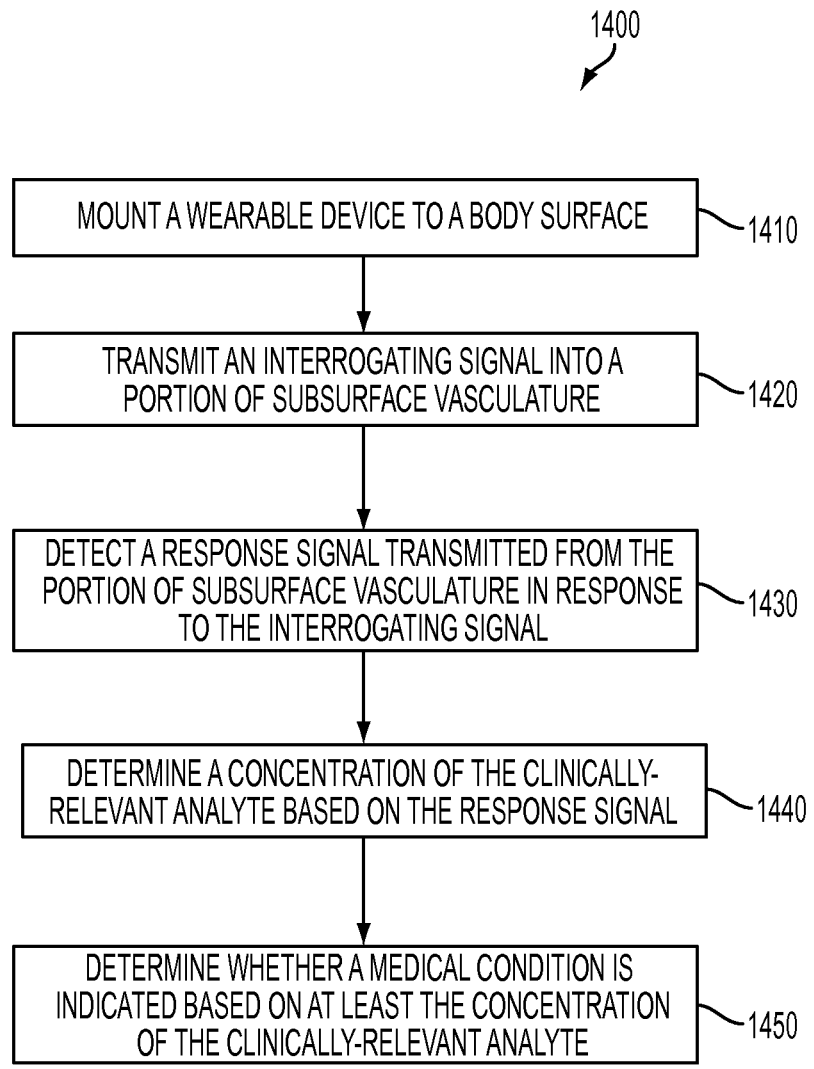
FIG. 14 is a flowchart of an example method for operating a wearable device.

FIG. 14 is a flowchart of a method 1400 for operating a wearable device to take non-invasive, in vivo, real-time measurements of physiological parameters. A wearable device is first mounted to a body surface of a human subject, wherein the body surface is proximate to a portion of subsurface vasculature (1410). In some examples, the wearable device, via a signal source, transmits an interrogating signal into the portion of subsurface vasculature (1420). The wearable device, via a detector, then detects a response signal transmitted from the portion of subsurface vasculature, wherein the response signal is related to binding of a clinically-relevant analyte to superparticles present in a lumen of the subsurface vasculature (1430). In some examples, the response signal is generated in response to an interrogating signal. The superparticles are configured to bind to the clinically-relevant analyte and comprise one or more types of targeting entities such as an antibody or an aptamer. The term "bind" is understood in its broadest sense to also include any detectable interaction between the clinically relevant analyte and the superparticles. The wearable device then determines the presence, absence and/or a concentration of the clinically-relevant analyte based on the response signal (1440) and whether a medical condition is indicated based on at least the presence, absence and/or concentration of the clinically-relevant analyte (1450). Further, in examples where the superparticles are magnetic, the wearable device may further direct a magnetic field into the portion of subsurface vasculature, the magnetic field being sufficient to cause the magnetic superparticles to collect in a lumen of the portion of subsurface vasculature.

Figure 15A:
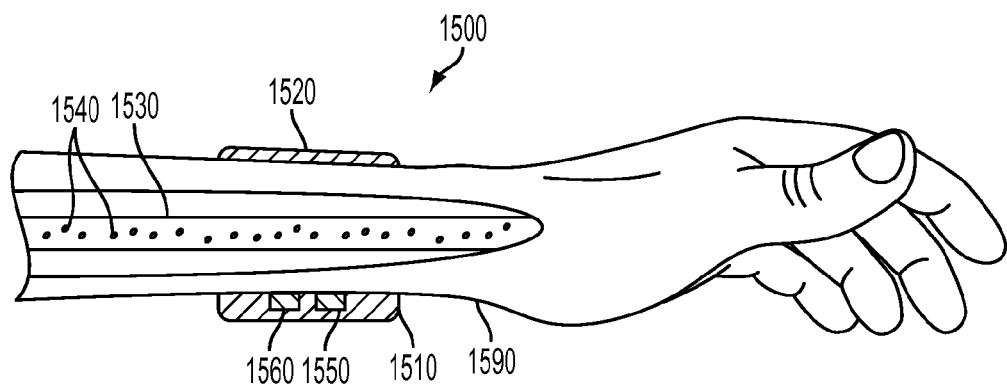
FIG. 15A is side partial cross-sectional view of an example wrist-mounted device, while on a human wrist.
Figure 15B:
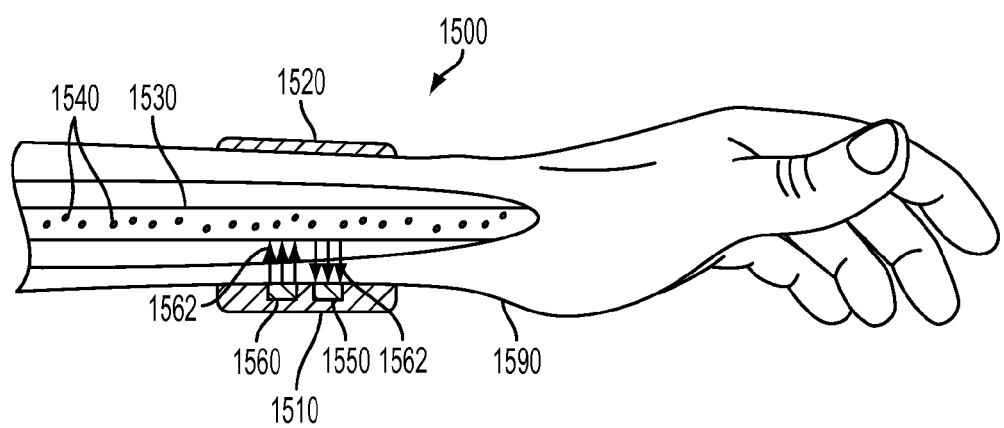
FIG. 15B is side partial cross-sectional view of an example wrist-mounted device, while on a human wrist.

FIGS. 15A-15B, 16A-16B, and 17A-17B are partial cross-sectional side views of a human wrist illustrating the operation of various examples of a wrist-mounted device. In the example shown in FIGS. 15A and 15B, the wrist-mounted device 1500 includes a measurement platform 1510 mounted on a strap or wrist-band 1520 and oriented on the anterior side 1590 of the wearer's wrist. Measurement platform 1510 is positioned over a portion of the wrist where subsurface vasculature 1530 is easily observable. Superparticles 1540 have been introduced into a lumen of the subsurface vasculature by one of the means discussed above. In this example, measurement platform 1510 includes a data collection system having both a detector 1550 and a signal source 1560. FIG. 15A illustrates the state of the subsurface vasculature when measurement device 1500 is inactive. The state of the subsurface vasculature during a measurement period is illustrated in FIG. 15B. At this time, signal source 1560 is transmitting an interrogating signal 1562 into the portion of subsurface vasculature and detector 1350 is receiving a response signal 1552 generated in response to the interrogating signal 1562. The response signal 1552 is related to the binding of a clinically relevant analyte present in the subsurface vasculature to the superparticles 1540. As described above, in some embodiments, an interrogating signal may not be necessary to generate a response signal related to the binding of an analyte to the superparticles.

Figure 16A:
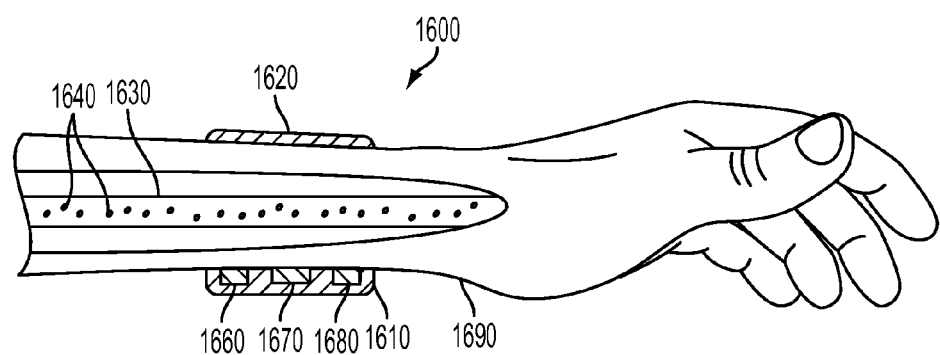
FIG. 16A is side partial cross-sectional view of an example wrist-mounted device, while on a human wrist.
Figure 16B:
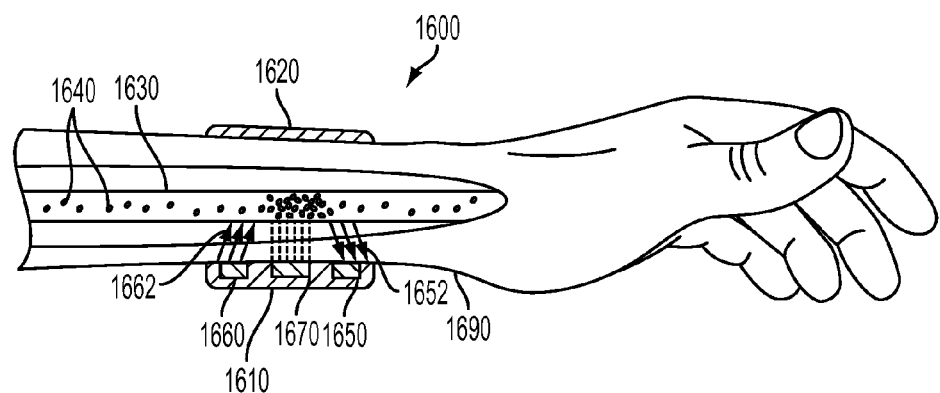
FIG. 16B is side partial cross-sectional view of an example wrist-mounted device, while on a human wrist.

Similar to the system depicted in FIGS. 15A and 15B, FIGS. 16A and 16B illustrate a wrist-mounted device 1600 including a measurement platform 1610 mounted on a strap or wristband 1620 and oriented on the anterior side 1690 of the wearer's wrist. In this example, measurement platform 1610 includes a data collection system having a detector 1650, a signal source 1660 and a collection magnet 1670. FIG. 16A illustrates the state of the subsurface vasculature when measurement device 1600 is inactive. The state of the subsurface vasculature when measurement device 1600 is active during a measurement period is illustrated in FIG. 16B. At this time, collection magnet 1670 generates a magnetic field 1672 sufficient to cause magnetic superparticles 1640 present in a lumen of the subsurface vasculature 1630 to collection in a region proximal to the magnet 1670. Signal source 1660 transmits an interrogating signal 1662 into the portion of subsurface vasculature and detector 1650 is receiving a response signal 1652 generated in response to the interrogating signal 1662. The response signal 1652 is related to the binding of a clinically relevant analyte present in the subsurface vasculature to the magnetic superparticles 1640. As described above, in some embodiments, an interrogating signal may not be necessary to generate a response signal related to the binding of an analyte to the magnetic superparticles.

Figure 17A:
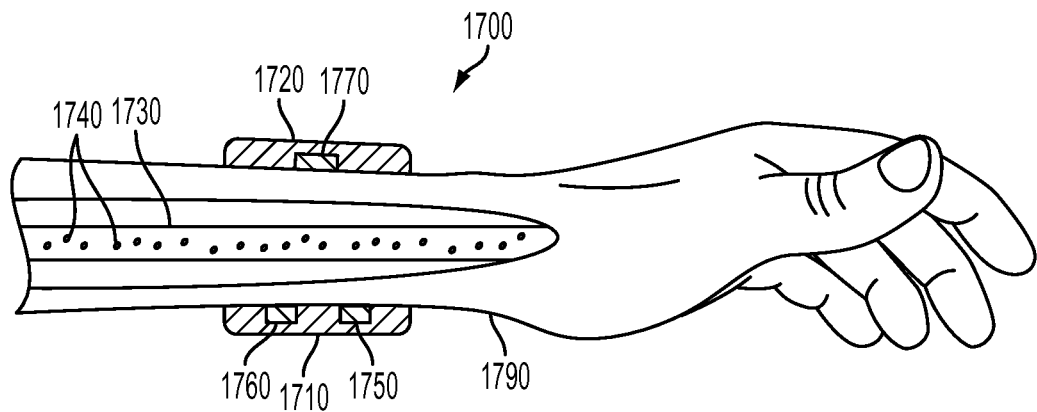
FIG. 17A is side partial cross-sectional view of an example wrist-mounted device, while on a human wrist.
Figure 17B:
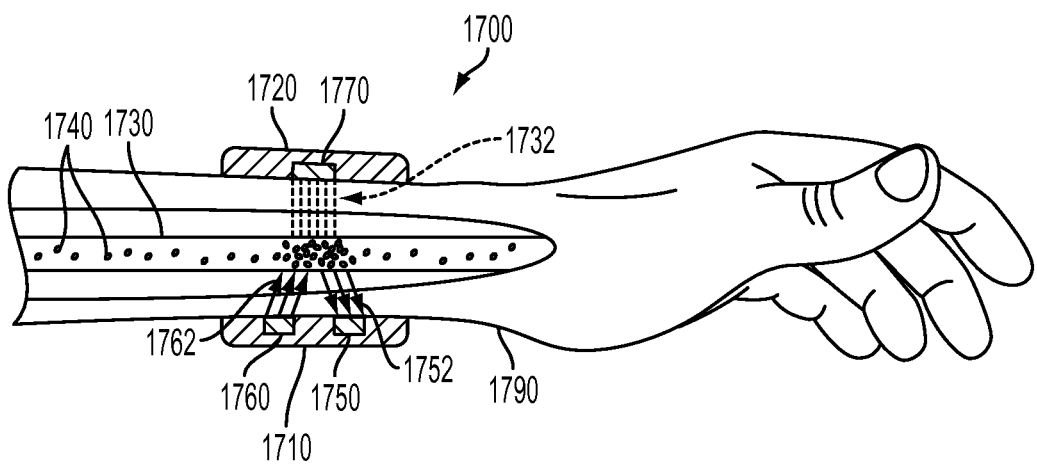
FIG. 17B is side partial cross-sectional view of an example wrist-mounted device, while on a human wrist.

FIGS. 17A and 17B illustrate a further embodiment of a wrist-mounted device 1700 having a measurement platform 1710 disposed on a strap 1720, wherein the detector 1750 and signal source 1760 are positioned on the posterior side 1790 of the wearer's wrist and the collection magnet 1770 is disposed on the anterior side 1780 of the wearer's wrist. Similar to the embodiments discussed above, FIG. 17A illustrates the state of the subsurface vasculature when measurement device 1700 is inactive. The state of the subsurface vasculature when measurement device 1700 is active during a measurement period is illustrated in FIG. 17B. At this time, collection magnet 1770 generates a magnetic field 1732 sufficient to cause magnetic superparticles 1740 present in a lumen of the subsurface vasculature 1730 to collection in a region proximal to the magnet 1770. Signal source 1760 transmits an interrogating signal 1762 into the portion of subsurface vasculature and detector 1750 is receiving a response signal 1752 generated in response to the interrogating signal 1762. The response signal 1752 is related to the binding of a clinically relevant analyte present in the subsurface vasculature to the magnetic superparticles 1740. As described above, in some embodiments, an interrogating signal may not be necessary to generate a response signal related to the binding of an analyte to the magnetic superparticles.

Both FIGS. 16B and 17B illustrate the path of the interrogating signal (1662, 1762) transmitted by the signal source (1660, 1760) and the responsive signal (1652, 1752) detected by the detector (1650, 1750) essentially overlapping over a portion of subsurface vasculature. In some examples, the signal source (1660, 1760) and the detector (1650, 1750) may be angled towards each other so that they are interrogating and detecting from essentially the same area of subsurface vasculature. However, in some instances, such as in the example shown in FIG. 14B, the paths of the interrogating signal (1662, 1762) transmitted by the signal source (1660, 1760) and the responsive signal (1652, 1752) detected by the detector (1650, 1750) may not overlap.

Figure 18:
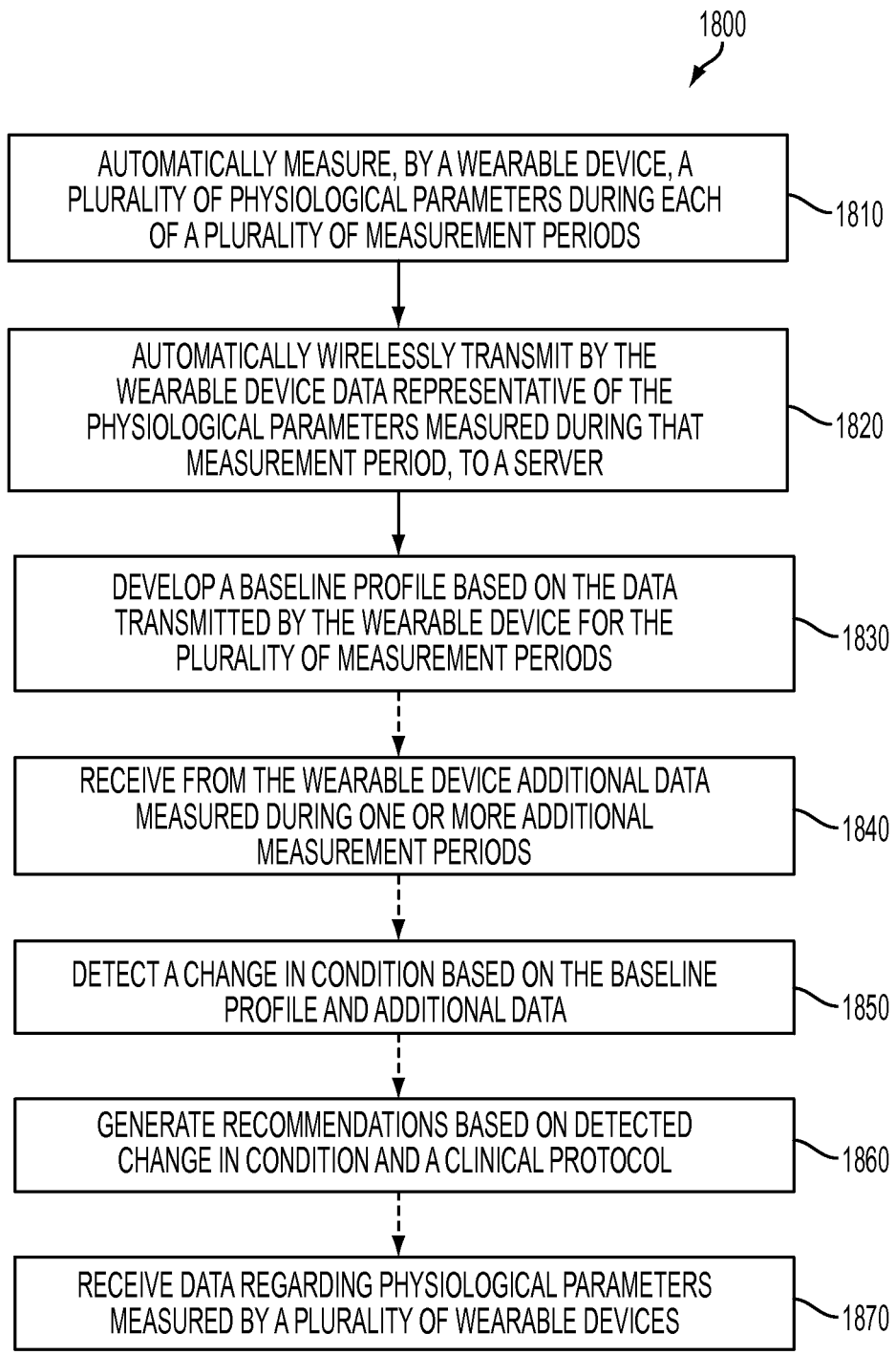
FIG. 18 is a flowchart of an example method for using a wearable device to take real-time, high-density, non-invasive, in vivo measurements of physiological parameters.

VI. Illustrative Methods for Real-Time, High-Density Physiological Data Collection Using a Wrist Mounted Device FIG. 18 is a flowchart of a method 1800 for using a wearable device to take real-time, high-density, non-invasive, in vivo measurements of physiological parameters. In a first step, the wearable device automatically measures one or more physiological parameters during each of a plurality of measurement periods (1810). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (1820). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (1830). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods (1840). The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (1850). The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol (1860). For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices (1870) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (1870) and provide an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 19:
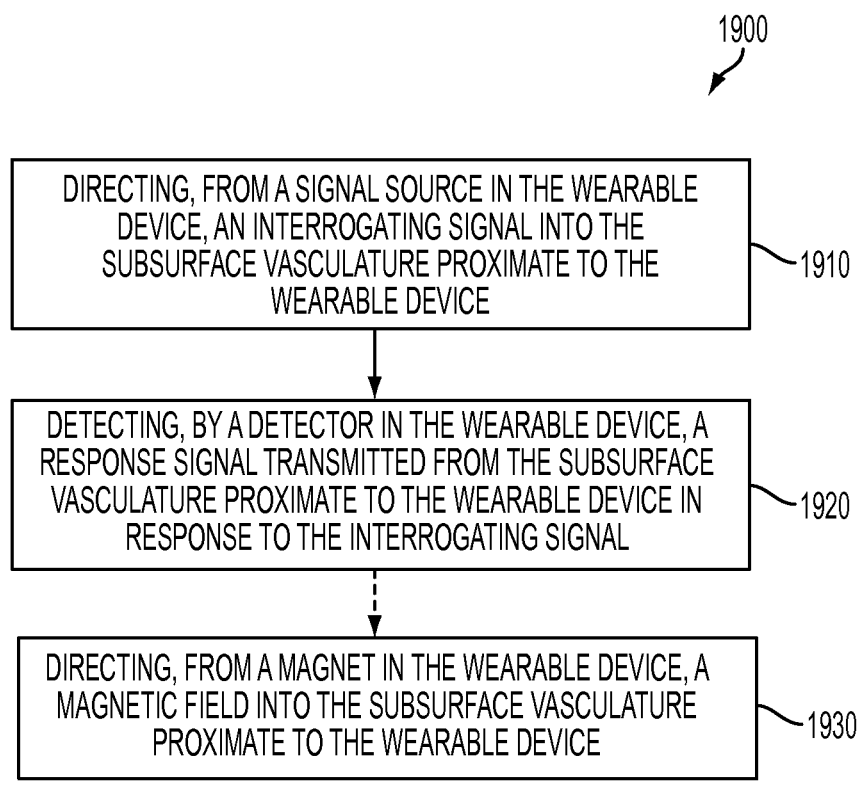
FIG. 19 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing superparticles into the blood, wherein the magnetic superparticles are configured to bind to the one or more analytes. As shown in FIG. 19, the wearable device may non-invasively measure one or more analytes in blood circulating in subsurface vasculature proximate to the wearable device by directing, from a signal source in the wearable device, an interrogating signal into the subsurface vasculature proximate to the wearable device (1910). As discussed above, this step may not be necessary in cases where the superparticles generate a response signal related to binding of the one or more analytes without the need for an interrogating signal. In any case, the wearable device may detect, with a detector, a response signal transmitted from the subsurface vasculature proximate to the wearable device in response to the interrogating signal (1920). The response signal is related to binding of the one or more analytes to the superparticles. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the superparticles also include a fluorophore, the response signal may include fluorescence radiation transmitted by the fluorophore in response to the interrogating signal.

In some examples, the superparticles may also be magnetic. The process of measuring one or more analytes in blood circulating in subsurface vasculature may further include directing, from a magnet in the wearable device, a magnetic field into the subsurface vasculature proximate to the wearable device (1930). The magnetic field is sufficient to cause the magnetic superparticles to collect in a lumen of the subsurface vasculature proximate to the wearable device.

Figure 20:
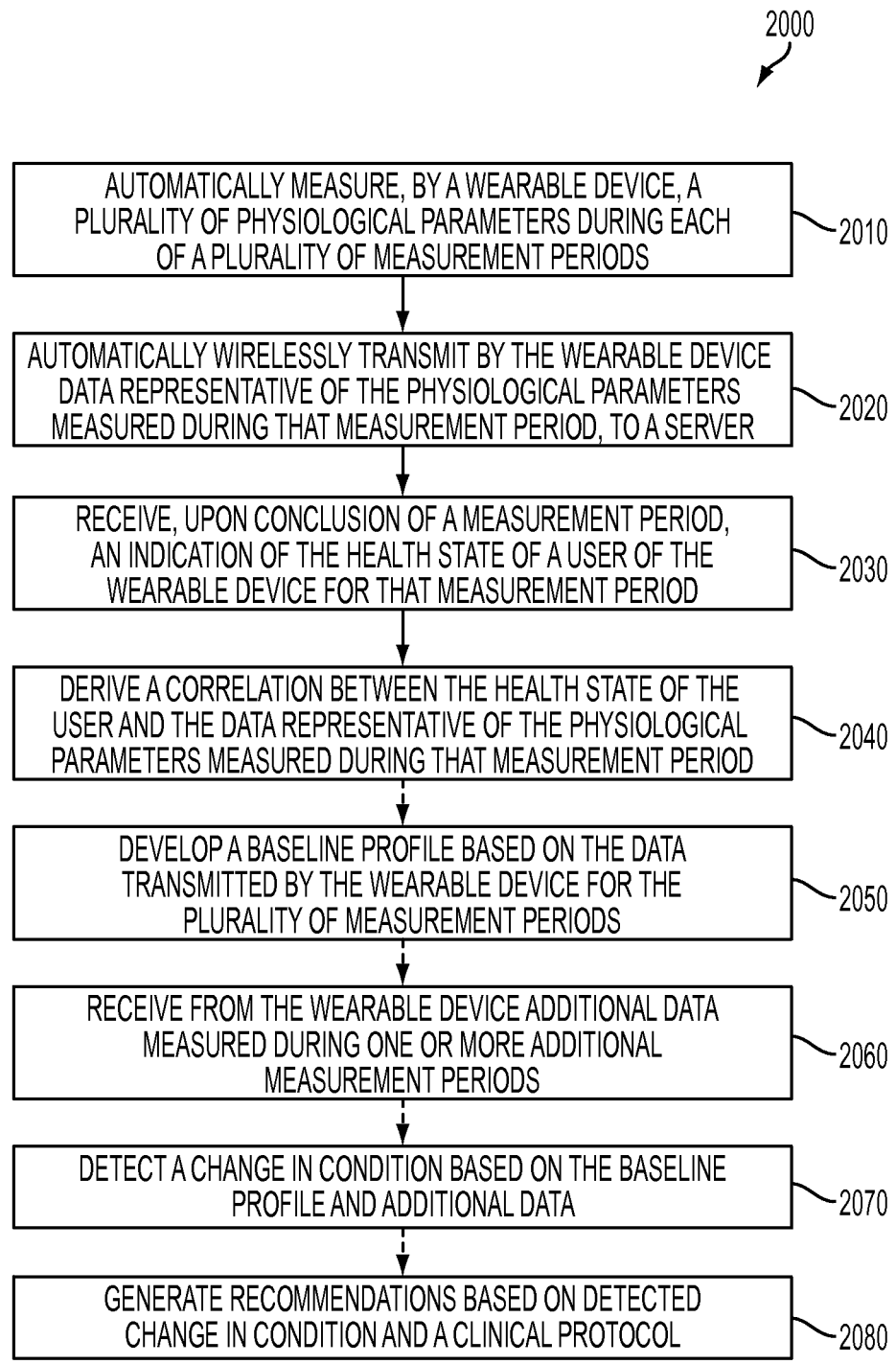
FIG. 20 is a flowchart of an example method for using a wearable device to take real-time, high-density, non-invasive, in vivo measurements of physiological parameters.

FIG. 20 is a flowchart of a method 2000 for using a wearable device to take real-time, high-density, non-invasive, in vivo measurements of physiological parameters. In a first step, the wearable device automatically measures one or more physiological parameters during each of a plurality of measurement periods (2010). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (2020). The server may be configured to receive, upon conclusion of a measurement period, an indication of the health state of a user of the wearable device for that measurement period (2030) and derive a correlation between the health state of the user and the data representative of the physiological parameters measured during that measurement period (2040). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlations to alert the user that a medical condition may be imminent.

A baseline profile may be developed by the server based on the data transmitted by the wearable device for the plurality of measurement periods (2050). The server may further be configured to receive from the wearable device additional data representative of the physiological parameters measured during one or more additional measurement periods (2060), detect a change in condition based on the baseline profile and the additional data (2070), and generate one or more recommendations based on the detected change in condition and a clinical protocol (2080). The clinical protocol may be developed based, at least in part, on the derived correlation. For example, the clinical protocol may indicate that a medical condition may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

VII. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A method for preparing molded composite particles, the method comprising the steps of:
   (a) casting a liquid solution of magnetic nanoparticles of at least one type, reporter labels of at least one type, targeting entities of at least one type and polymer matrix precursors into a mold, the mold including a plurality of nanowells;
   (b) thermally annealing the magnetic nanoparticles in the liquid cast solution in the wells;
   (c) exposing the liquid cast solution to a curing stimulus to form the molded composite particles; and
   (d) recovering the molded composite particles from the mold.

2. The method according to claim 1, wherein the liquid polymer matrix precursors are UV, heat, or pH curable.

3. The method according to claim 1, wherein step (b) is performed in the presence of a permanent magnet.

4. The method according to claim 2, wherein the amount of nanoparticles in the liquid casting solution ranges from 0.1% to 70% (w/w).

5. The method according to claim 4, wherein the amount of nanoparticles in the liquid casting solution ranges from 1% to 50% (w/w).

\* \* \* \* \*